United States Patent [19]

Fréchet et al.

[11] Patent Number: 5,041,516

[45] Date of Patent: Aug. 20, 1991

[54] DENDRITIC MOLECULES AND METHOD OF PRODUCTION

[75] Inventors: Jean M.J. Fréchet; Craig J. Hawker; Athena E. Philippides, all of Ithaca, N.Y.

[73] Assignee: Cornell Research Foundation, Inc., Ithaca, N.Y.

[21] Appl. No.: 369,270

[22] Filed: Jun. 21, 1989

[51] Int. Cl.$^5$ ............... C08G 18/00; C08G 63/00; C08G 64/00; C08G 65/00

[52] U.S. Cl. .................................. 528/44; 528/45; 528/68; 528/70; 528/74; 528/85; 528/271; 528/272; 528/310; 528/323; 528/332; 528/363; 528/370; 528/425

[58] Field of Search ............... 528/425, 310, 323, 44, 528/45, 68, 70, 74, 85, 271, 272, 332, 363, 370

[56] References Cited

U.S. PATENT DOCUMENTS

| | | | |
|---|---|---|---|
| 4,507,466 | 3/1985 | Tomalia et al. | 528/363 |
| 4,558,120 | 12/1985 | Tomalia et al. | 528/332 |
| 4,568,737 | 2/1986 | Tomalia et al. | 528/363 |
| 4,587,329 | 5/1986 | Tomalia et al. | 528/374 |
| 4,631,337 | 12/1986 | Tomalia et al. | 528/391 |
| 4,694,064 | 9/1987 | Tomalia et al. | 528/350 |
| 4,737,550 | 4/1988 | Tomalia | 528/374 |
| 4,857,599 | 8/1989 | Tomalia et al. | 525/309 |
| 4,871,779 | 10/1989 | Killat et al. | 521/28 |

*Primary Examiner*—John Kight, III
*Assistant Examiner*—Rabon Sergent
*Attorney, Agent, or Firm*—Bruce F. Jacobs

[57] ABSTRACT

Dendritic macromolecules and a novel convergent process for producing the same are disclosed. The convergent process enables the accurate control and design of the surface functionality of the macromolecule.

52 Claims, No Drawings

DENDRITIC MOLECULES AND METHOD OF PRODUCTION

BACKGROUND OF THE INVENTION

1. Field of the Invention

The present invention is directed to the preparation of dendritic macromolecules having controlled surface functionality by a novel convergent approach. Once prepared, the dendritic molecules are used to prepare new macromolecular assemblies with unusual architectures and properties.

2. Description of the Prior Art

Interest in dendritic molecules dates back to the early fifties with the publication of a theoretical paper by Flory, J., Am. Chem. Soc., 74, 2719(1952) stating, "Highly branched polymer molecules may be synthesized without incidence of gelation through the use of monomers having one functional group of one kind and two or more of another capable of reacting with the former." Few examples of purposeful attempts to control molecular constitution through this approach were investigated until the late 1970's when Vogtle and coworkers, Synthesis 155 (1978), described a "cascade" approach to branched oligomeric products through a Michael-type addition of a polyfunctional amine to acrylonitrile followed by reduction of the newly formed nitrile chain ends to yield a next generation of reactive amine groups.

Although interesting, this approach has not been extended beyond a product having a molecular weight of 790 Daltons. A subsequent attempt, described in U.S. Pat. No. 4,289,872, involved a stepwise protection-deprotection approach for the condensation of lysine into highly branched high molecular weight products for which little characterization data was made available. More recently, Newkome used a nucleophilic displacement reaction on a multifunctional core to produce, after two stages of reaction, a cascade molecule coined "arborol" with molecular weights of up to 1600. See, for example, Aharoni et al, Macromolecules 15, 1093 (1982); J. Org. Chem. 50, 2004 (1985); Newkome et al, J. Chem. Soc. Chem. Commun., 752 (1986); and Newkome et al, J. Am. Chem. Soc. 108, 849 (1986).

The most extensive published studies of dendritic molecules are directed to the "starburst" polymers. See, for example, U.S. Pat. Nos. 4,507,466; 4,558,120; 4,568,737; 4,587,329; and 4,737,550. Such "starburst" polymers are produced by allowing a polyfunctional amine core molecule to react with excess methyl acrylate in a Michael-type addition. Each arm of the resulting star-branched molecule is then reactivated to an amineterminated moiety by exhaustive amidation using excess 1,2-diaminoethane to afford a chain extended product in which each primary amino group becomes a new branch point in the next series of Michael additions.

"Starburst" polymers may also be made using pentaerythritol or an analogous triol as the core moiety from which a highly branched polyether starburst polymer may be built in successive deprotection-alkylation steps.

Kim et al, Polymer Preprints, 29 (2), 310 (1988) describe the synthesis of a hyperbranched polyphenylene with a molecular weight of up to 4,000 by aryl-coupling reaction. In this procedure, growth is irregular, affording a product mixture with high polydispersity.

In all but the last of these approaches for producing dendritic molecules, a polyfunctional reactive core was used to initiate dendritic growth and the radially grown interior layers carried on their outer surface a very large number of reactive functionalities. This is referred to as a "divergent" approach for producing dendritic molecules. The use of such highly functionalized cores provides for extremely efficient growth. For example, from a tetrafunctional core and tetrafunctional monomer, Hall and Tomalia, J. Organic Chemistry, 52, 5305 (1987) prepared in only three iterations ("generations") polyethers containing nominally 108 surface functional groups. However, such a high packing density appears to prevent further regular growth. In fact, with all systems in which growth requires the reaction of large numbers of surface functional groups, it is difficult to ensure that all will react at each growth step. This poses a significant problem in the synthesis of regular monodispersed and highly organized structures since unreacted species may lead to failure sequences or spurious reactivity at later stages of the stepwise growth sequence.

Although great strides have been made in the control of polymer structures through the development of new living polymerization or the use of macromonomers or telechelic polymers, it is still very difficult to control the shape of macromoleculer assemblies and the spatial placement of reactive groups within their confines. In view of the high degree of order that such highly branched structures may exhibit, and the number of potentially interesting and novel molecular topologies that may be envisioned, the control of their surface functionality both in terms of the number and the placement of surface functional groups is an important target.

SUMMARY OF THE INVENTION

According to the present invention, a "convergent" pathway for the growth of dendritic polymers is employed to provide access to the accurate placement of one or more functional groups "X" on the outer surface of macromolecules, such as those shown in formulas 1-3:

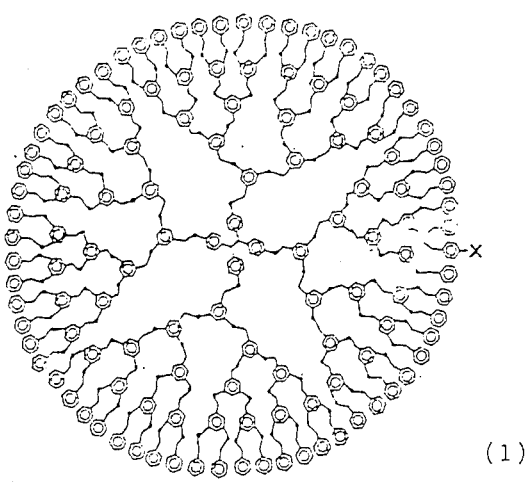

(1)

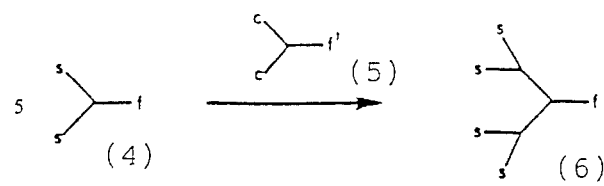

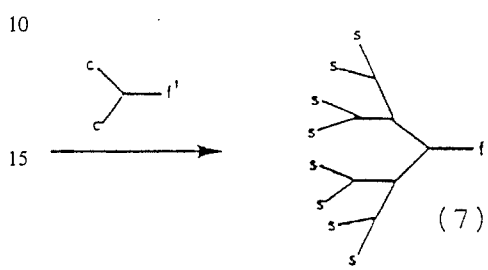

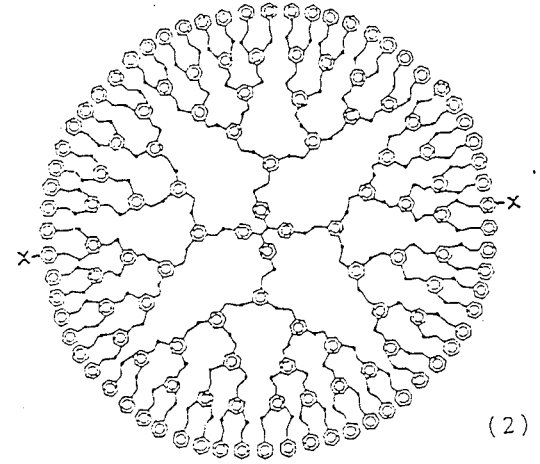

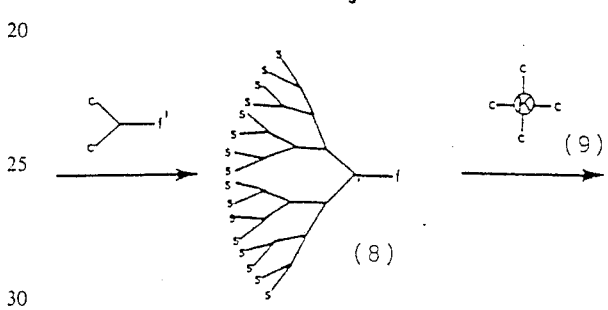

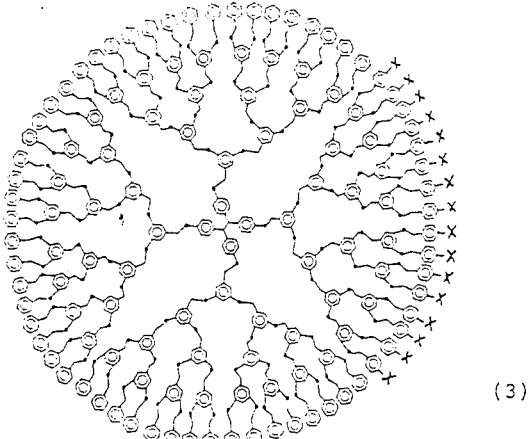

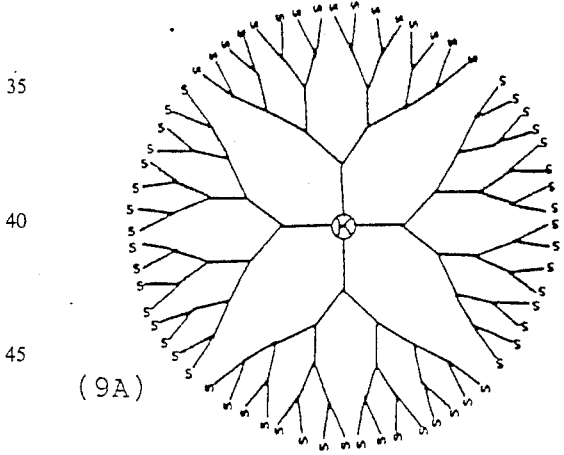

The convergent approach to building macromolecules involves building the final molecule by beginning at its periphery, rather than at its core as in the prior art divergent processes.

At each step of the convergent process, growth is designed to occur at a single site, i.e. the "focal point" of the growing dendrimer. This avoids the problems encountered in some prior art approaches in which growth involved simultaneous additions at progressively larger numbers of sites. The process can also produce macromolecules containing no reactive surface functionalization, i.e. the surface groups are H or phenyl, as in the prior art "starburst" polymers.

The convergent process may be represented by the following general reaction scheme:

Starting compound (4) contains what will eventually constitute the surface "s" of the dendritic molecule as well as a reactive functional group "f" which is condensed with monomer (5). Each of the surface groups "s" may contain one or more reactive but non-reacting functional groups "X." The X's are non-reacting with all of the compounds and reagents used to form the dendritic macromolecules and all intermediates formed, but they are readily reactive with numerous other chemical groups in known manner. The monomer itself has two coupling groups "c" and a protected functional group "f'." After coupling, "f'" is activated to "f" and the process is continued by successive iterations until the dendritic wedge (8) is obtained. Dendrimer (8) has a single reactive group "f" at its focal point which may be coupled to a polyfunctional core, such as (9), with three other dendrimers to provide the final dendritic sphere (9A) with exactly 64 "s" surface groups in only four iterations. As used herein, in a "dendrimer" is any highly branched polymer chain.

The "focal point" of a dendritic molecule is the geometric location (or point) towards which all of the branches converge. Since a dendritic molecule is by definition "tree-like," the focal point would be like the base of the trunk of a very regular tree (where all the branches converge and the tree is "attached" to the ground. The focal reactive group is the chemical entity located at the focal point of the dendritic molecule and capable of undergoing a coupling reaction directly or indirectly after activation.

One of the attractive features of the "convergent" process of this invention is that appropriate manipulations of coupling steps may be used to produce not only non-functional molecules and molecules having uniform surface functionalization wherein all of the "s" groups are identical as in the prior art, but also non-uniformly functionalized molecules with only one, two or n functional groups on their outer surface. These non-uniform structures are not achievable by prior art "core-first" or "divergent" processes. Moreover, the non-uniformity of functionalization may be in the number of functional groups, the type of functional groups, the reactivity thereof, or any combination of these. This invention enables the preparation of structures having no functional groups, or a single functional group, or multiple copies of the same functional group, or two or more different functional groups on the same molecule. Thus, a drug delivery system can be produced by attaching a targeted antibody to one type of a surface functional group of the dendritic structure and a drug to all other surface functional groups. The structures produced by the convergent process are very highly monodisperse, making them particularly suitable for medical applications in which reproducible uniformity is often critical. In other drug delivery systems, the drug can be attached to appropriate surface functional groups of the dendritic macromolecule. Alternatively it can be located inside a generally hollow spheroidal dendritic macromolecule and released slowly by diffusion. Or the drug may be bound by hydrolyzable bonds and be released slowly (time-release).

The accurate control of surface functionalization may be used in a variety of ways. For example, dendritic fragments can be prepared by this convergent process and then coupled into large spheroid shaped macromolecules which would owe their properties to their unusual topologies and their non-uniform surface functionalization. The dendritic fragments which are joined together to form the macromolecule do not have to be identical fragments. As a result, great variability in and control over the specific surface functionality is achieved.

The dendritic fragments, preferably those having no surface functionalization or only a limited number of one or two types of surface functionalization, may also be linked to one another and to other molecules by a variety of reactions to produce novel topological macromolecule systems such as those containing spheroidal and linear fragments, "barbell" shapes, "knots" or "star" structures originating from a spherical knot, etc.

For instance, if structure 2 is prepared in which each X is cyano (X=CN), the cyano groups can be hydrolyzed to —COOH and then reacted with a suitable dialcohol (either monomeric like 1,4-butanediol or polymeric like a bis hydroxy-terminated polyester or polystyrene) to form a polymer having "knots" of the dendritic macromolecule linked by the organic portion of the dialcohol. In this case the dendritic macromolecule is functioning as a conventional di-carboxylic acid co-monomer or reactive oligomer. Or if the dendritic macromolecule has only a single cyano group, then a "barbell" structure would result.

The control of surface functionality is also important because it imparts unique properties to the final products that permit their further use in conventional chemical reactions as is normally available only to much smaller "normal" organic molecules. Particular applications of this type include their use as crosslinking reagents, cores for star-polymer growth, and monomers and comonomers in the production of polymers.

The macromolecules of the present invention made by the convergent process will have novel properties resulting from their unusual topology, their uniform small size of generally up to about 100 Angstroms, preferrably between about 20 and 100 Angstroms, the uniformity or non-uniformity of the surface functionality, the possible existence of strong molecular dipoles and the possible presence of chirality. These novel macromolecules are expected to have use in the areas of agents to control the rheology of polymer melts, solutions, or coatings, crosslinking agents, substrates for preparing star polymers, drug delivery systems, regularly sized particles for applications involving quantum confinement effects, materials for optoelectronics and non-linear optics, molecular dipoles, carriers for synthetic enzymes, carriers for catalysts, carriers for genetic material, standards for molecular weight measurements, standards for electron or other forms of advanced microscopy, standards for sizing of small particles, models for globular proteins and other globular materials, agent to control the density of polymers or coatings, toughening agents, compatibilizers for polymer blends, and the like.

The only limiting factor on how large a dendritic molecule can be prepared while using the convergent process would be steric hindrance which could occur if the dendrimer units became too large to allow full reaction with the monomer unit or appropriate core molecules. However, any steric hindrance problems can be readily overcome with the convergent process, unlike with the divergent prior art processes, merely by including spacer units, i.e. longer chain aliphatic moieties, either in some of the iteration/generations or in all of the monomer units which are used to build the molecule.

DESCRIPTION OF THE PREFERRED EMBODIMENTS

According to one of the preferred embodiments of the present invention, the convergent process is used to produce a non-surface functional dendrimer according to the following reaction sequence (II):

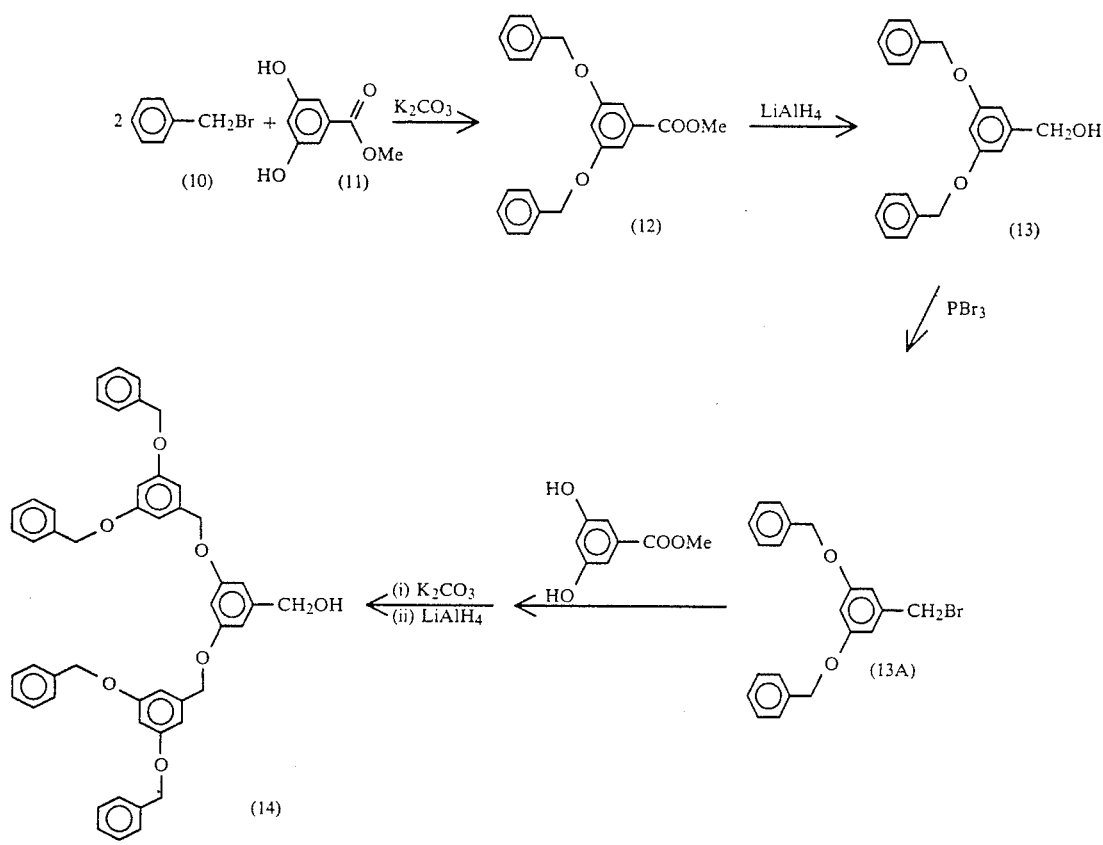

As shown, a non-functional surface compound, benzyl bromide (10), the benzyl group of which will eventually be located at the surface of the spheroidal dendritic macromolecule such as the one shown in Formula (1), is reacted with a monomer unit (11), methyl 3,5-dihydroxybenzoate. The coupling reaction which takes place results in the benzylation of the monomer unit's two phenolic hydroxyls. This benzylation results in the formation of the first generation dendrimer (12) which contains an ester group as the latent reactive group located in the focal position. Activation of the latent coupling site is effected through its transformation into the corresponding benzylic alcohol (13) and eventually the reactive bromide (13a). The bromination reaction can be carried out in yields of well over 90% using $CBr_4$ and triphenylphosphine or phosphorous tribromide. Further growth to the second generation dendrimer (14) involves a sequential repetition of the previous steps with the creation of progressively larger molecules having a single benzylic halide group at their focal point for subsequent reaction with the monomer unit. This procedure can then be used to produce even larger dendrimers of the 3rd, 4th, 5th, etc. generations by a sequential repetition of Reaction Sequence II. Any of the dendrimers so formed may then be coupled to a polyfunctional core to form a macromolecule..

For example, a dendrimer of the formula:

(15)

may be formed by four successive repetitions of Reaction Sequence (II) and is therefore referred to herein as a 4th generation-$CH_2Br$. The dendrimer of formula (15) having a molecular weight of 3,351 may then be coupled to a trifunctional core such as a compound of the formula:

(16)

by heating at reflux a mixture of (16), (15), potassium carbonate, and 18-crown-6 in dry acetone or dioxane. 18-crown-6 is a cyclic ether compound which is used to solubilize the potassium carbonate into the organic solvent in a conventional manner. The result, after purification by extraction and chromatography is a pure dendritic macromolecule of the formula:

(17)

having a molecular weight of 10,116 and being represented by the empirical formula $C_{671}H_{576}O_{93}$.

The dendritic macromolecule of formula (17) is, of course, only one of endless possible macromolecules that may be formed by the convergent process of this invention. This molecule contains no surface functionalization that could be readily used in subsequent reactions of the macromolecule. The formula of the dendritic macromolecule will be determined by the selection of a specific surface compound with or without reactive but non-reacting functionality, reactive monomer unit, and polyfunctional core, as well as the number of "generations" used to form the macromolecule. Each of the basic components must be selected while taking into account the reactivities of the groups present on the other components used to build the specific molecule since both the reactivity and non-reactivity of the various building blocks is critical to the use of the convergent process of this invention.

Surface compounds useful herein are those compounds having either of the general formulas:

$(s)_m—R—f$ or $(s)_m—R—f'$ wherein "s" represents a group which will form the surface of the resultant molecule and is non-reacting with any portion of itself, other surface compounds, the reactive monomer units being used, the polyfunctional core, and all reagents and intermediates formed in the preparation of the dendritic macromolecule; "m" is an integer, preferably 1, 2 or 3; "R" is any organic moiety which is non-reacting with all other compounds and reagents used and intermediates formed in the preparation of the dendritic macromolecule; "f" is a group which does not react with the "s" groups but does react with group "c" of a reactive monomer unit; and "f'" is a non-reacting group which is activatable to a reacting "f" group. The "s" group is optionally substituted with one or more "X" reactive functional groups which are also non-reacting with all of the compounds and reagents used and intermediates formed in constructing the dendritic molecule. The terms "reacting" and "non-reacting" as used herein refer to the conditions under which the various chemical groups come in contact with each other during the process and not necessarily in the absolute sense. Thus a group which is deemed "non-reacting" if it does not react under normal conditions, even if extraordinary steps could force a reaction to occur.

The specific functionalities "X" which can be placed at the surface of the dendritic molecule are limited only by the requirement that they not be reactive with each other or with any compound or reagent used to build the molecule or any intermediate generated in the building. Thus their selection will depend upon the specific compounds chosen used to build the specific molecule desired. Examples of surface functionality which can be provided on the surfaces of the dendritic macromolecules include such as F, Cl, Br, CN, $—NO_2$, $—NHC(O)R^2$ wherein $R^2$ can be alkyl, aryl, O-alkyl, or O-aryl, $—CONH_2$, $—CO_2R^3$ wherein $R^3$ is alkyl or aryl, $—O—C(O)R^3$, $—OR^3$, and alkyl or aryl groups substituted with any of the above functionality. A particularly desirable surface functionality group is cyano because it can be readily converted into a carboxylic acid, a carbamide, an aldehyde, or even an alkene.

Monomer units which may be used in the present invention are those of the general formula:

$(c)_n—R'—f'$ wherein "c" is a coupling group which is non-reacting with "f" but reactive with the activated "f" group; "n" is an integer greater than 1, preferably 2 or 3; R' is selected from the same moieties as R and may be either the same as R or different; "c" or "f" or "f'"; "f'" is a non-reacting group which is activatable to reacting group "f". If desired, different monomer units can be employed in successive iterations/generations used to build the macromolecule. Reaction sequence VII below shows the use of such different monomer units. The monomer unit thus has "n" coupling sites and one focal non-reactive but activatable focal group "f'". Thus the r'th generation of a dendritic wedge contains $n^r$ surface compounds which may be the same or different.

Specific monomer units which may be used in the present invention include such as:

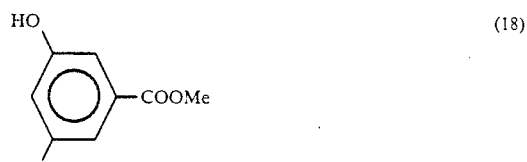
(18)

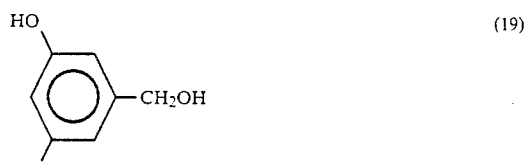
(19)

(20)

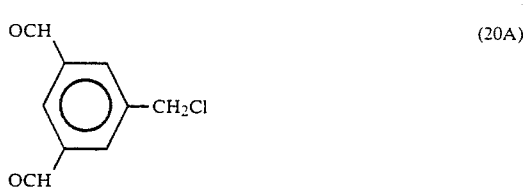
(20A)

As indicated, the non-reacting "f'" group on the monomer units must be such that it can be converted to an activated "f" group, either directly or through a series of reactions. Examples of suitable activated "f" groups include acid, aldehyde, alcohol, amine, phenol, halide, thiol, isocyanate, isothiocyanate, aryl halide, activated ester, alkene, and ketone. Thus, examples of suitable pairs of non-reacting "f'" and reacting "f" groups and any intermediates required include:

|   | "f'" group | intermediate | "f" group |
| --- | --- | --- | --- |
| a. | ester | alcohol | bromine |
| b. | aldehyde | alcohol | bromine |
| c. | carbamate | amine | isocyanate |
| d. | ester | — | acid |
| e. | carbamate | — | amine |
| f. | aryl ester | — | phenol |

To convert a non-reacting ester "f'" group to an alcohol intermediate, the ester in dry tetrahydrofuran (THF) can be added dropwise to a solution of lithium aluminum hydride in dry THF and the mixture refluxed for about an hour, followed by cooling, hydrolysis with aqueous sodium hydroxide, isolation by solvent extraction, and purification as required. To convert this alcohol intermediate to a reacting bromine "f" group, a mixture of it with carbon tetrabromide can be dissolved in dry THF and triphenylphosphine added with stirring at room temperature under nitrogen, followed by isolation and purification.

To convert a non-reacting aldehyde "f'" group to an alcohol intermediate, the aldehyde and tetra-n-butyl ammonium borohydride can be dissolved in dry chloroform, stirred at room temperature under nitrogen for about 24 hours, followed by hydrolysis with aqueous hydrogen peroxide (3%), isolation by solvent extraction and purification as needed. The alcohol intermediate can then be converted to a reacting bromine as above.

These, as well as all other such conversions required, entail only the use of conventional organic chemistry techniques which are individually well known from the literature, and thus not further exemplified herein.

The methyl 3,5-dihydroxybenzoate and 3,5-dihydroxybenzaldehyde monomer units are presently preferred since neither is subject to any troublesome side reactions since both possess electron withdrawing substituents which are not prone to C-alkylation.

Polyfunctional cores which may be used in the present invention have the general formula:

$$(c)_x—R''''$$

wherein "c" is a protected or unprotected coupling group which is non-reacting with "f" but reacting with the activated "f" group; "x" is an integer greater than 1, preferably greater than 2; and "R''''" is any organic moiety selected from the same moieties as R and R' and may be the same or different as either.

Thus the core compound is a polyfunctional molecule having 2 or more nucleophilic or electrophilic groups. Examples of such groups include alcohol, amino, phenol, thiol, thiophenol, halide, and carboxylic acid. The core may also be a polymer containing many such groups, e.g. a Novolak or a poly(p-hydroxystyrene) or cellulose, or a copolymer containing such groups on only one of the comonomers. Specific monomeric polyfunctional cores which may be used include such as:

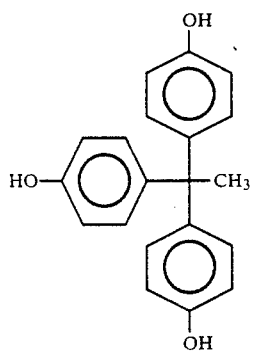 (16)

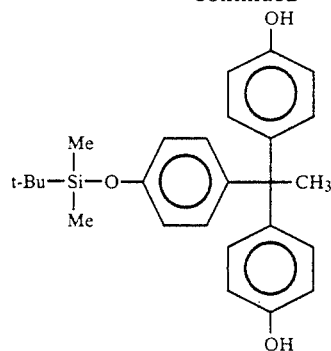 (22)

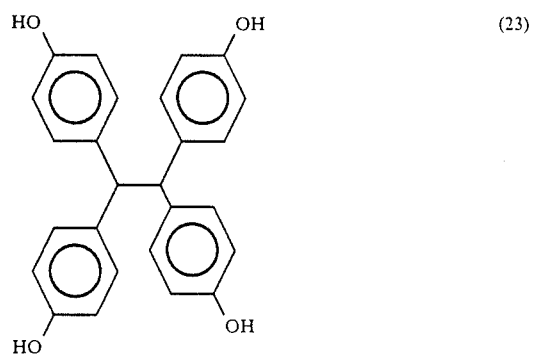 (23)

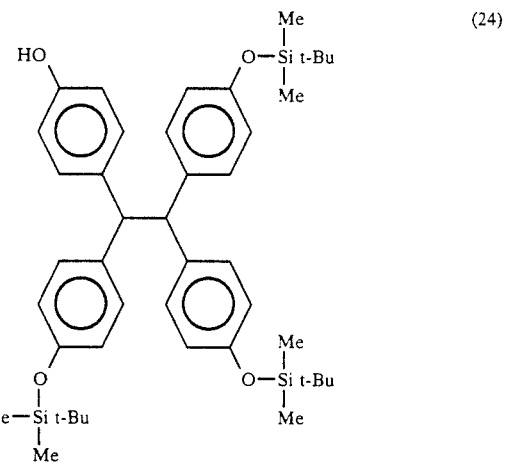 (24)

as well as pentaerythritol, pyromellitic anhydride, glucose, phloroglucinol, pyromellitic acid, benzenetetracarboxylic acid or anhydride, ethylenediamine, and the like. As shown by Compounds (22) and (24), one or more of the "c" groups of the polyfunctional core may be protected with a group which must be removed to make the "c" reactive, i.e. it is activable to a reactive "c" group.

The use of "protected" core molecules greatly increases the synthetic and practical ease with which dendritic molecules having non-uniform surface functionality are synthesized by attaching differed dendritic wedges to a single core.

As can be seen from the formulas of suitable surface compounds, monomer units, and polyfunctional cores, the specific composition of each, for a particular dendritic macromolecule, is dependent upon the others since the basis for selection is the reactivity and non-reactivity of the various "s," "X," "c," "f," and "f'" groups, as well as the non-reactivity of the various organic moieties "R," "R'," and "R"," and not the specific chemical composition of any one of them.

The primary reaction used in the building of the dendritic macromolecules is that between the "c" coupling group of the monomer unit or the polyfunctional core (which may be the same or different) and the reactive "f" of the surface compound or the growing dendritic wedge which has been formed. Examples of suitable pairs of "c" and "f" groups and the linkage formed therebetween which may be used in the present invention include:

|    | "c" group  | "f" group | linkage formed |
|----|------------|-----------|----------------|
| a. | hydroxyl   | bromine   | ether          |
| b. | isocyanate | alcohol   | carbamate      |
| c. | acid       | hydroxyl  | ester          |
| d. | hydroxyl   | acid      | ester          |
| e. | acid       | amine     | amide          |
| f. | bromide    | hydroxyl  | ether          |
| g. | amine      | bromide   | amine          |
| h. | alkene     | thiol     | thioether      |

As was shown in Reaction Sequence I, the convergent growth approach yields dendrimers which are characterized by the presence of two different zones of functionalization: the focal reactive group "f" and the optional surface functionalization "X". Coupling of several dendrimers to a central core through reaction of the focal reactive groups produces a spheroidal dendritic macromolecule in which no focal functionality remains. See, for example, macromolecules (1)–(3) and (17). One of the important advantages of the convergent process is the ability to introduce and control the surface functionality of a dendritic macromolecule. Introduction of surface functionalities "X" may be achieved in several ways.

If a uniform type of surface functionality is desired, it is best achieved by an appropriate selection of the alkylating agent in the formation of the first generation dendrimer (25) (reaction sequence IV):

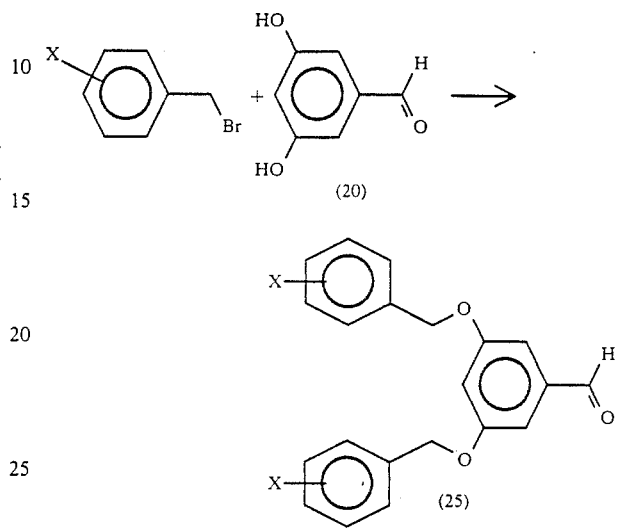

in which X is as defined above.

If only a limited number of such functional "X" groups are desired in the final product, i.e. a compound similar to (15), but with only one surface functional group "X" at the surface, it can be prepared as shown in reaction sequence V:

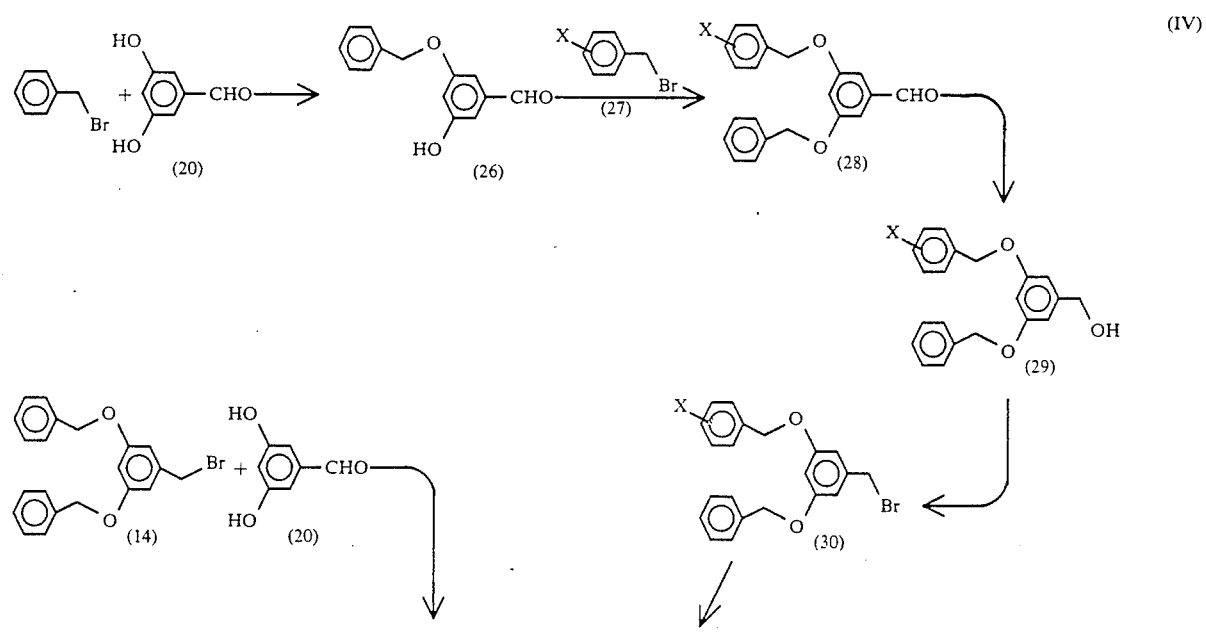

(IV)

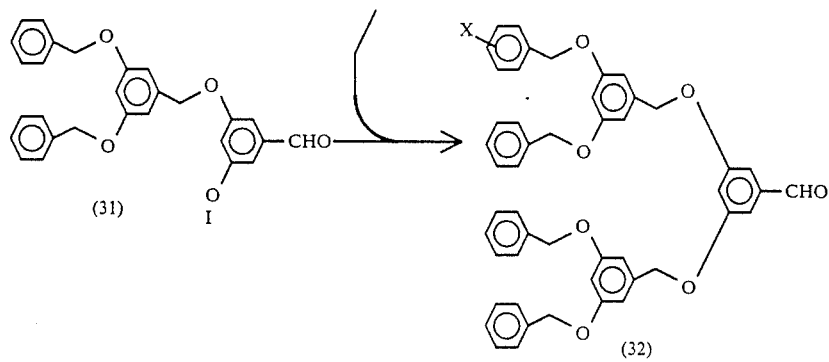

In this reaction sequence both mono- and di- O-alkylated monomers are required at various stages of the preparation in order to obtain the non-uniform structures. In this reaction the monoalkylation of 3,5-dihydroxybenzaldehyde with the compound (14) proceeds to about 80% when a mixture of (14), (20), potassium carbonate, and 18-crown-6 is heated at reflux in dry dioxane. Condensation of benzyl bromide with an appropriate excess of monomer (20) affords compound (26) which is easily separated from the reaction mixture and is then alkylated with an X-substituted benzylic bromide (27) (where X is as defined above) to afford the non-uniformly substituted first generation dendrimer (28) which can be activated to the bromide (30) in high yield steps requiring no intermediate purification. The non-uniform first generation dendrimer (14) is then used to alkylate monomer (20) under conditions, which favor monoalkylation to produce compound (31). It has been observed that the presence of a free phenolic group on moieties such as (26) or (31) greatly facilitates their separation from the reaction mixture. Condensation of (30) with (31) affords the monofunctionalized second generation dendrimer (32). This sequence of steps may be continued until a molecule of the desired size is formed such as a fourth generation dendrimer (33) which may then be coupled to a protected core molecule (24) as shown in reaction sequence VI:

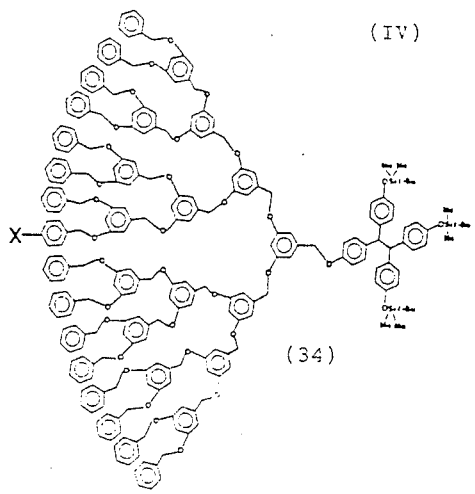

The core of macromolecule (34) is then stripped of the silicon-containing protecting groups using a fluoride anion and the macromolecule may then be reacted with, for example, three molecules of symmetrical dendrimer (15) to produce monofunctionalized and mondispersed spherical molecules of formula (1).

Alternatively, the second generation dendrimer (32) may be activated for further coupling by reduction and bromination. The sequence of steps described above may be repeated until a third generation dendrimer (35) having a single cyano group on its outer surface is formed. Final assembly to a polyfunctional core (21) can be done in two steps (if there were difficulty in removing the core protecting group in the presence of a particular surface functionality), shown in reaction sequence VI A:

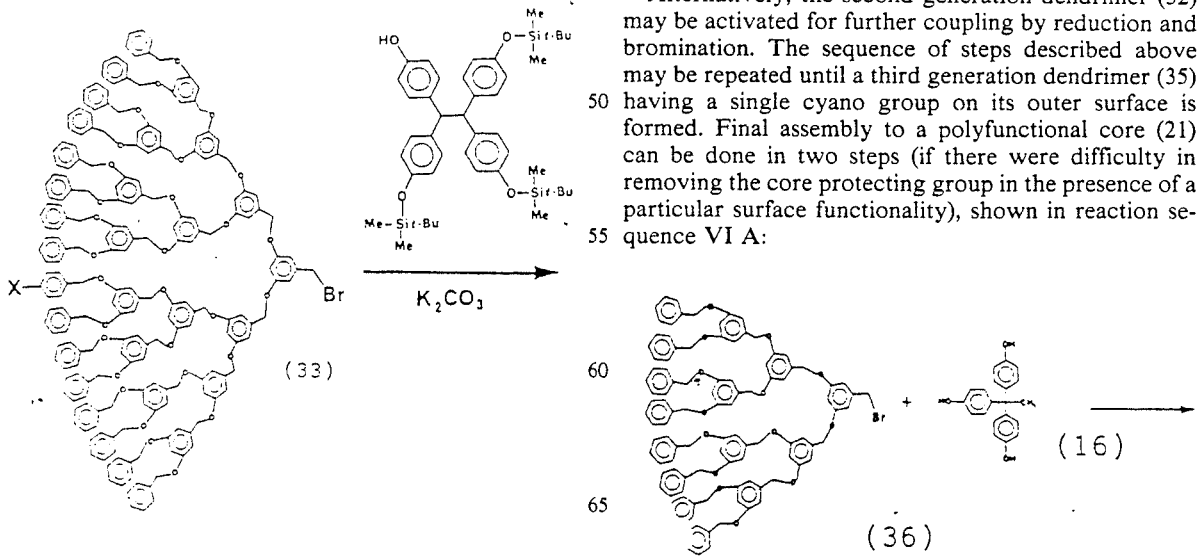

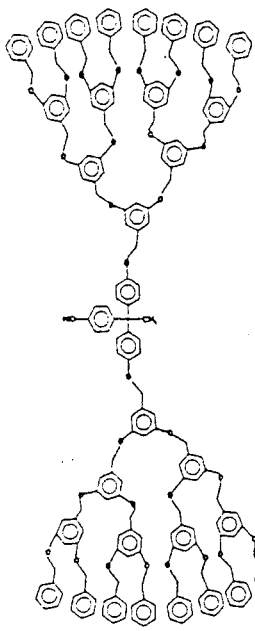

(VIA)

(37)

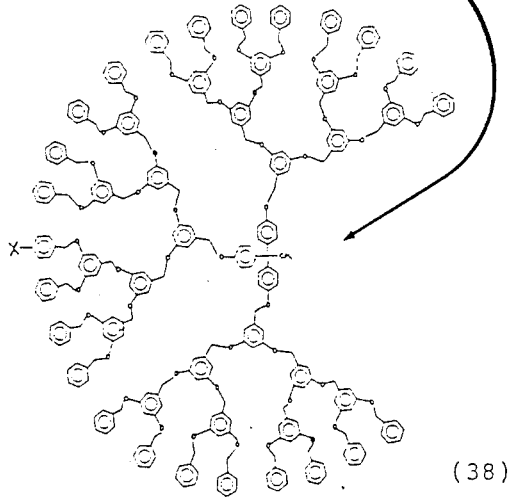

(38)

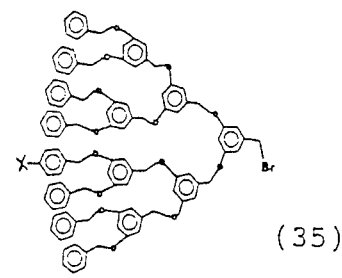

(35)

In the first step, two molecules of symmetrical third generation dendrimers (36) are coupled to the core to produce a product containing one remaining free phenolic hydroxyl group (37). This free hydroxyl group of (37) is then used to couple to the unsymmetrical third-generation dendrimer (35) to produce a spheroidal dendritic macromolecule (38) having only one functional group on its surface.

This general procedure can be used to produce an unlimited number of different macromolecules with different surface functional groups by the judicious selection of appropriate starting materials and by the use of protected and unprotected cores which enable the design of the final product.

With some synthetic targets, i.e. dendritic macromolecules with alternating generations (layers) of functional groups such as (39B) where generations of ether and urethane functional groups alternate, it may be possible to greatly accelerate the reaction sequence described above by using a different monomer at every other step of the sythesis as shown in reaction sequence VII:

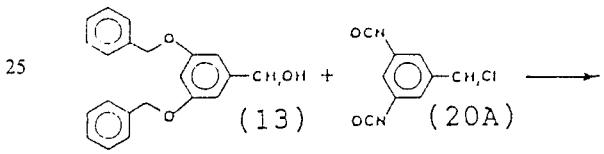

(VII)

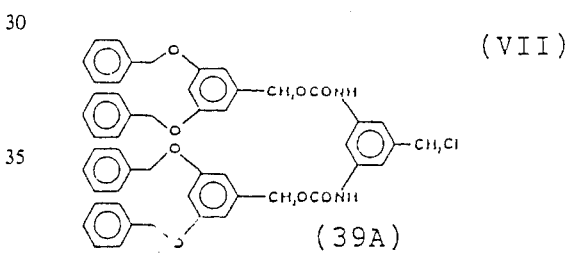

(39A)

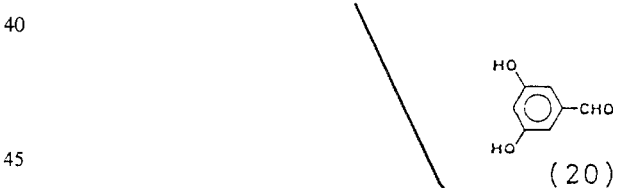

(20)

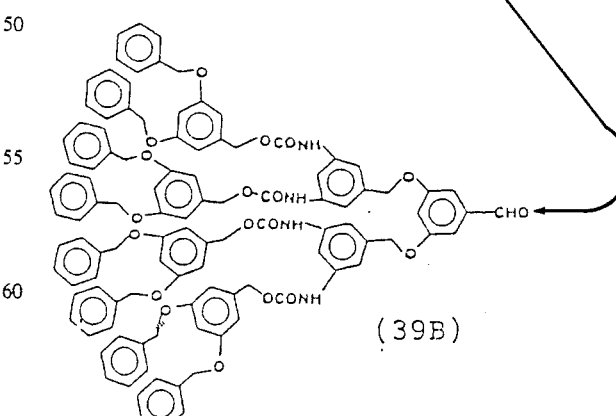

(39B)

For example, a third generation dendrimer (39B) could be prepared by the one-pot condensation of the first generation dendrimer (13) with alpha-chloro-3,5-toluene di-isocyanate (20A) followed by in situ reaction of benzylic halide (39A) with monomer (20). If repeated sequentially, this procedure will allow the rapid preparation of a fifth generation dendrimer with only two intermediate isolations.

Still another possible reaction sequence, using an amide monomer linkage, is shown in Reaction Sequence VIII:

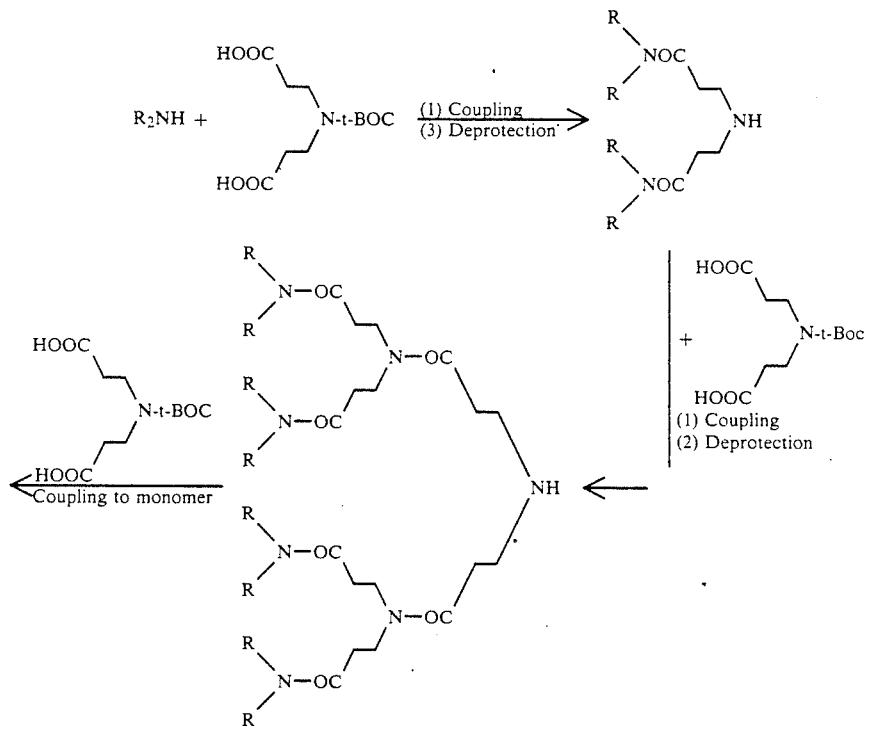

wherein $R_2NH$ functions as the surface compound $(s)_m$—R—f in which the R groups are "s," "m" is 2, the N is the "R," and the H is "f". As before, the only requirement for the R groups is that they be chemically inert under the conditions used for the coupling and deprotection steps. Thus the R groups can be, e.g. a 2, 3, or 4-halophenyl groups, substituted aliphatic or aromatic hydrocarbons, peptide fragments, and amino acids which are protected. As shown, this convergent synthesis involves the formation of amide linkages using N-t-BOC-iminodipropionic acid. Alternative processes such as alkylation may also be used.

The convergent process for producing dendritic macromolecules as described above will now be further exemplified by the following non-limiting examples in which all parts and percents are by weight unless otherwise specified.

EXAMPLE I

In this example, the following abbreviations are used for ease of reference:

| | |
|---|---|
| Ph = | Phenyl group ($C_6H_5$—) |
| BzBr = | Benzyl bromide (formula $PhCH_2Br$) |
| DBzB = | 3,5-Dibenzyloxy benzyl group (formula: 3,5-$(PhCH_2O)_2C_6H_3CH_2$—) |
| DBzBA = | 3,5-Dibenzyloxy benzyl alcohol (formula: 3,5-$(PhCH_2O)_2C_6H_3CH_2OH$) |
| DBzBBr = | 3,5-Dibenzyloxy benzyl bromide (formula: 3,5-$(PhCH_2O)_2C_6H_3CH_2Br$) |
| DBzBE = | Methyl 3,5-Dibenzyloxybenzoate (formula: 3,5-$(PhCH_2O)_2C_6H_3CO_2Me$) |
| DHBE = | Methyl 3,5-Dihydroxybenzoate (formula: 3,5-$(HO)_2C_6H_3CO_2Me$) |
| DOB = | 3,5-Dioxybenzyl group (formula: 3,5-$(-O)_2C_6H_3CH_2$—) |
| DOBA = | 3,5-Dioxybenzyl alcohol group (formula: 3,5-$(-O)_2C_6H_3CH_2OH$) |
| DOBBr = | 3,5-Dioxybenzyl bromide group (formula: 3,5-$(-O)_2C_6H_3CH_2Br$) |
| DOBE = | Methyl 3,5-Dioxybenzoate group (formula: 3,5-$(-O)_2C_6H_3CO_2Me$) |
| LAH = | Lithium aluminium hydride ($LiAlH_4$) |
| THF = | Tetrahydrofuran |
| THPE = | 1,1,1-Tris(4-hydroxyphenyl)ethane, core molecule formula ($HOC_6H_4)_3CCH_3$) |
| TOPE = | 1,1,1-Tris(4-oxyphenyl)ethane, core group (formula ($-OC_6H_4)_3CCH_3$) |

The following outline describes in brief the procedure for producing the dendrimers and the macromolecules described in this Example. A detailed procedure follows the outline.

Generation 1
(1) DHBE + 2BzBr → DBzBE (Compound I)
(2) DBzBE + LAH → DBzBA (Compound II)
(3) DBzBA + $PBr_3$ → DBzBBr (Compound III)

Generation 2
(1) DHBE + 2DBzBBr → $(DBzB)_2$DOBE (Compound IV)
(2) $(DBzB)_2$DOBE + LAH → $(DBzB)_2$DOBA (Compound V)
(3) $(DBzB)_2$DOBA + $PBr_3$ → $(DBzB)_2$DOBBr (Compound VI)

-continued

Generation 3
(1) DHBE + 2(DBzB)$_2$DOBBr → (DBzB)$_4$(DOB)$_2$DOBE (Compound VII)
(2) (DBzB)$_4$(DOB)$_2$DOBE + LAH → (DBzB)$_4$(DOB)$_2$DOBA (Compound VIII)
(3) (DBzB)$_4$(DOB)$_2$DOBA + PBr$_3$ → (DBzB)$_4$(DOB)$_2$DOBBr (Compound IX)

Generation 4
(1) DHBE + 2(DBzB)$_4$(DOB)$_2$DOBBr → (DBzB)$_8$(DOB)$_4$(DOB)$_2$ DOBE (Compound X)
(2) (DBzB)$_8$(DOB)$_4$(DOB)$_2$DOBE + LAH → (DBzB)$_8$(DOB)$_4$-(DOB)$_2$DOBA (Compound XI)
(3) (DBzB)$_8$(DOB)$_4$(DOB)$_2$DOBA + PBr$_3$ → (DBzB)$_8$(DOB)$_4$-(DOB)$_2$DOBBr (Compound XII)

Generation 5
(1) DHBE + 2(DBzB)$_8$(DOB)$_4$(DOB)$_2$DOBBr → (DBzB)$_{16}$-(DOB)$_8$(DOB)$_4$(DOB)$_2$DOBE (Compound XII)

Dendritic Macromolecules
(1) 3(DBzB)$_4$(DOB)$_2$DOBBr + THPE → (DBzB)$_{12}$(DOB)$_6$-(DOB)$_3$TOPE (Compound XIV)
(2) 3(DBzB)$_8$(DOB)$_4$(DOB)$_2$DOBBr + THPE → (DBzB)$_{24}$-(DOB)$_{12}$(DOB)$_6$(DOB)$_3$TOPE (Compound XV)

Preparation of Methyl 3,5-dihydroxybenzoate (DHBE, dendrimer unit)

To a solution of 3,5-dihydroxybenzoic acid (50.0 g, 320 mmol) in methanol (310 ml) was added concentrated sulfuric acid (7.7 ml) and the resultant solution heated at reflux for 16 hrs. It was then cooled and approximately 200 ml of methanol removed under reduced pressure. To the remaining solution was added water (300 ml) and the mixture extracted with ether (4×50 ml). The combined extracts were washed with saturated aqueous sodium bicarbonate (50 ml), dried, and evaporated to dryness. The resultant solid was recrystallized from 50 ml of methanol/125 ml of water to give methyl 3,5-dihydroxybenzoate as off-white crystals (50.1 g, 91.9%).

Generation 1

(1) Preparation of DBzBE—Compound I (Structure 12 in Description)

A mixture of DHBE (30.0 g, 179 mmol), BzBr (53.4 ml, 76.1 g, 445 mmol), and potassium carbonate (27.0 g, 195 mmol) was heated at reflux under argon in dry acetone (150 ml) for 20 hours. Thin layer chromatography showed very little DHBE or its mono-alkylated derivative. The reaction mixture was evaporated to dryness and the residue partitioned between chloroform/water. The aqueous layer was further extracted with chloroform (3×50 ml) and the combined chloroform extracts dried and evaporated to dryness. The residue was recrystallized from methanol (approx. 75 ml) to give 53.0 g of Compound I (85% based upon DHBE).

(2) Preparation of DBzBA—Compound II (Structure 13 in Description)

To a stirred suspension of LAH (5.9 g, 150 mmol) in dry THF (120 ml) was added dropwise DBzBE (41.0 g, 119 mmol) in dry THF (590 ml). After the addition was complete, the mixture was heated at reflux for 1 hour and cooled. An aqueous solution of sodium hydroxide (1M, 24 ml) was cautiously added to destroy excess LAH and the mixture heated at reflux for 1 hour. After cooling, the precipitate was filtered, washed thoroughly with THF (approx. 300 ml) and the combined filtrates evaporated to dryness. Crude product was recrystallized from 95% methanol/water to give 33.5 g of Compound II (89% based upon DBzBE).

(3) Preparation of DBzBBr—Compound III (Structure 14 in Description)

To a stirred solution of DBzBA (13.7 g, 43 mmol) in dry benzene (66 ml) was added phosphorous tribromide (1.48 ml, 4.22 g, 15 mmol) dropwise under argon while the solution was cooled in an ice bath. After addition, the solution was allowed to warm to room temperature and stirring continued for 150 minutes. Water (160 ml) was added, the solution reduced in volume to 160 ml, and extracted with chloroform (3×50 ml). The combined extracts were dried, evaporated to dryness, and the residue recrystallized from ether/hexane. The yield of the crystallized product, Compound III was 14.4 g (88% based upon DBzBA).

Generation 2

(1) Preparation of (DBzB)$_2$DOBE—Compound IV

This was prepared from DHBE (2.38 g, 14.2 mmol), DBzBBr (13.0 g, 34 mmol), and potassium carbonate (2.10 g, 15.2 mmol) in 100 ml of dry acetone. The procedure was the same as for DBzBE (Compound I). The crude product was recrystallized from ether/hexane to give 8.53 g of Compound IV (78% based upon DHBE).

(2) Preparation of (DBzB)$_2$DOBA—Compound V (Structure 15 in Description)

This was prepared from LAH (140 mg, 3.5 mmol) in dry THF (14 ml) and (DBzB)$_2$DOBE (2.1 g, 2.7 mmol) in dry THF (35 ml). The procedure was the same as for DBzBA (Compound II). The crude product was recrystallized from ether/hexane to give 1.83 g of Compound V (90% based upon (DBzB)$_2$DOBE).

(3) Preparation of (DBzB)$_2$DOBBr—Compound VI

This was prepared from (DBzB)$_2$DOBA (1.80 g, 2.4 mmol) in dry benzene (13 ml) and phosphorus tribromide (230 mg, 80 ul, 0.85 mmol) in dry benzene (5 ml). The procedure was the same as for DBzBBr (Compound III). The crude product was purified by flash chromatography eluting with chloroform to give 1.62 g of Compound VI (82% based upon (DBzB)$_2$DOBA).

Generation 3

(1) Preparation of (DBzB)$_4$(DOB)$_2$DOBE—Compound VII

This was prepared from DHBE (101 mg, 0.6 mmol), (DBzB)$_2$-DOBBr (1.21 g, 1.50 mmol), and potassium carbonate (120 mg, 0.90 mmol) in 60 ml of dry acetone. The procedure was the same as for DBzBE (Compound 1). The crude product was purified by flash chromatography eluting with 10% hexane/chloroform to give 911 mg of Compound VII (94% based upon DHBE).

(2) Preparation of (DBzB)$_4$(DOB)$_2$DOBA—Compound VIII

This was prepared from LAH (30 mg, 0.75 mmol) in dry THF (5 ml) and (DBzB)$_4$(DOB)$_2$DOBE (850 mg, 0.52 mmol) in dry THF (10 ml). The procedure was the same as for DBzBA (Compound II). The crude product was purified by flash chromatography eluting with chloroform to give 74.4 mg of Compound VIII (89% based upon (DBzB)$_4$(DOB)$_2$(DOBE).

(3) Preparation of (DBzB)$_4$(DOB)$_2$DOBBr—Compound IX

This was prepared from (DBzB)$_4$(DOB)$_2$DOBA (804 mg, 0.50 mmol) in dry benzene (10 ml) and phosphorous tribromide (48 mg, 16 ul, 0.18 mmol) in dry benzene (3 ml). The procedure was the same as for DBzBBr (Compound III). The crude product was purified by flash chromatography eluting with 10% hexane/chloroform to give 446 mg of Compound IX (54% based upon (DBzB)$_4$(DOB)$_2$-DOBA).

Generation 4

(1) Preparation of (DBzB)$_8$(DOB)$_4$(DOB)$_2$DOBE—Compound X

A mixture of DHBE (13.5 mg, 0.08 mmol), (DBzB)$_4$(DOB)$_2$-DOBBr (331 mg, 0.20 mmol), and potassium carbonate (16.5 mg, 0.12 mmol) was heated at reflux under argon in dry acetone (15 ml) for 20 hours. The reaction was evaporated to dryness and the residue partitioned between chloroform/water. The aqueous layer was extracted with chloroform (3×20 ml) and the combined chloroform extracts dried and evaporated to dryness. The residue was purified by flash chromatography eluting with chloroform then 1% ethylacetate/chloroform to give 250 mg of Compound X (94% based upon initial amount of DHBE).

(2) Preparation of (DBzB)$_8$(DOB)$_4$(DOB)$_2$DOBA—Compound XI

This was prepared from LAH (6 mg, 0.158 mmol) in dry THF (5 ml) and (DBzB)$_8$(DOB)$_4$(DOB)$_2$DOBE (270 mg, 0.081 mmol) in dry THF (5 ml). The procedure was the same as for DBzBA Compound II). The crude product was purified by flash chromatography eluting with 1% ethylacetate/chloroform to give 200 mg of Compound XI (76% based upon (DBzB)$_8$(DOB)$_4$(DOB)$_2$DOBE).

(3) Preparation of (DBzB)$_8$(DOB)$_4$(DOB)$_2$DOBBr—Compound XII

This was prepared from (DBzB)$_8$(DOB)$_4$(DOB)$_2$DOBA (210 mg, 0.064 mmol) in dry benzene (3 ml) and phosphorus tribromide (6.1 mg, 2.1 ul, 0.023 mmol) in dry benzene (1 ml). The procedure was the same as for DBzBBr (Compound III). The crude product was purified by flash chromatography eluting with chloroform to give 140 mg of Compound XII (65% based on (DBzB)$_8$-(DOB)$_4$(DOB)$_2$DOBA).

Generation 5

(1) Preparation of (DBzB)$_{16}$(DOB)$_8$(DOB)$_4$(DOB)$_2$DOBE—Compound XIII

This was prepared from DHBE (1.0 mg, 0.006 mmol), (DBzB)$_8$(DOB)$_4$(DOB)$_2$DOBBr (50 mg, 0.015 mmol), and potassium carbonate (1.1 mg, 0.007 mmol) in 5 ml of dry acetone. After 20 hours further DHBE (3.0 mg, 1.8 mmol) was added. The procedure was the same as for Compound X. The crude product was purified by flash chromatography eluting with chloroform then 1% ethylacetate/chloroform to give 36 mg of Compound XIII (90% based upon initial amount of DHBE).

Preparation of Dendritic Macromolecule (1) Preparation of (DBzB)$_{12}$(DOB)$_6$(DOB)$_3$TOPE—Compound XIV A mixture of THPE (2.1 mg, 0.007 mmol), (DBzB)$_4$(DBO)$_2$-DOBBr (Compound IX) (40 mg, 0.030 mmol) in 5 ml of dry acetone was heated at reflux under argon for 20 hours. Thin layer chromatography showed only product and unreacted (DBzB)$_4$(DBO)$_2$-DOBBr. A further amount of THPE (6.3 mg, 0.021 mmol) was added and the mixture heated at reflux for 2 hours. The reaction was evaporated to dryness and the residue partitioned between chloroform/water. The aqueous layer was extracted with chloroform (3×10 ml) and the combined organic phase dried and evaporated to dryness. The residue was purified by preparative thin layer chromatography eluting with 1% ethyl acetate/chloroform to give 28 mg of Compound XIV (84% based upon initial amount of THPE).

(2) Preparation of (DBzB)$_{24}$(DOB)$_{12}$(DOB)$_6$(DOB)$_3$TOPE—Compound XV (Structure 17 in Description)

This was prepared from THPE (1.22 mg, 0.0040 mmol), (DBzB)$_8$(DOB)$_4$(DOB)$_2$DOBBr (Compound XI) (50 mg, 0.015 mmol), and potassium carbonate (1.0 mg, 0.0067 mmol) in dry acetone (5 ml). After 20 hours further THPE (3.7 mg, 0.012 mmol) was added. The procedure was the same as for Compound XIV. The crude product was purified by preparative thin layer chromatography eluting with 1% ethylacetate/chloroform to give 35 mg of Compound XV (86% based on initial amount of THPE).

EXAMPLE II

Preparation of a Monofunctionalized Dendritic Macromolecule

In this example, the following abbreviations are used:

BzCBzB = 3-Benzyloxy-5(4-cyanobenzyloxy)benzyl group (3-(PhCH$_2$O)-5-(NCC$_6$H$_4$O)C$_6$H$_3$CH$_2$-)

BzCBzBA = 3-Benzyloxy-5(4-cyanobenzyloxy)benzyl alcohol (3-(PhCH$_2$O)-5-(NCC$_6$H$_4$OC$_6$H$_3$CH$_2$OH)

BzCBzBBr = 3-Benzyloxy-5-(4-cyanobenzyloxy)benzyl bromide (3-(PhCHO)-5-(NCC$_6$H$_4$O)C$_6$H$_3$CH$_2$Br)

BzCBzBD = 3-Benzyloxy-5-(4-cyanobenzyloxy)benzaldehyde (3-(PhCH$_2$O)-5-(NCC$_6$H$_4$O)C$_6$H$_3$CHO)

BzHBD = 3-Benzyloxy-5-hydroxy benzaldehyde (3-(PhCH$_2$O)-5-OHC$_6$H$_3$CHO)

CBzBr = 4-cyanobenzyl bromide (4-NCC$_6$H$_4$CH$_2$Br)

DHBD = 3,5-Dihydroxy benzaldehyde group (3,5-(HO)$_2$C$_6$H$_3$CHO)

DOBD = 3,5-Dioxy benzaldehyde group (3,5-(-O)$_2$C$_6$H$_3$CHO)

HOBD = 3-hydroxy-5-oxybenzaldehyde group (3-HO-5-(-O)C$_6$H$_3$CHO)

TSHPE = 1,1,2-Tris(4-t-butydimethylsilyloxy phenyl)-2-(4-hydroxyphenyl)ethane, a triprotected CORE molecule OTHPE = 1-(4-oxyphenyl)-1,2,2-Tris-(4-hydroxyphenyl) ethane group TEOPE = 1,1,2,2-Tetrakis(4-oxyphenyl)ethane group DOHPE = 1,1-Di(4-oxyphenyl)-1-(4-hydroxyphenyl)ethane In summary outline, the procedure described in detail below can be formulated as follows:

---

Generation 1

(1) DHBD + BzBr → BzHBD (Compound XVI)

(2) BzHBD + CBzBr → BzCBzBD (Compound XVII)

-continued (3) BzCBzBD + NaBH₄ → BzCBzBA (Compound XVIII)
(4) BzCBzBA + PBr₃ → BzCBzBBr (Compound XIX)

Generation 2
(1) DHBD + DBzBBr → (DBzB)HOBD (Compound XX)
(2) (DBzB)HOBD + BzCBzBBr → (DBzB)(BzCBzB)DOBD (Compound XXI)
(3) (DBzB)(BzCBzB)DOBD + NaBH4 → (DBzB)(BzCBzB)DOBA (Compound XXII)
(4) (DBzB)(BzCBzB)DOBA + PBr₃ → (DBzB)(BzCBzB)DOBBr (Compound XXIII)

Generation 3
(1) DHBD + (DBzB)₂DOBBr → [(DBzB)₂DOB]HOBD (Compound XXIV)
(2) [(DBzB)₂DOB]HOBD + (DBzB)(BzCBzB)DOBBr → (DBzB)₃-(BzCBzB)(DOB)₂DOBD (Compound XXV)
(3) (DBzB)₃(BzCBzB)(DOB)₂DOBD + (nBu)₄NBH₄ → (DBzB)₃(BzCBzB)(DOB)₂-DOBA (Compound XXVI)
(4) (DBzB)₃(BzCBzB)(DOB)₂DOBA + CBr₄/PPh₃ → (DBzB)₃(BzCBzB)(DOB)₂-DOBBr (Compound XXVII)

Generation 4
(1) DHBD + (DBzB)₄(DOB)₄DOBBr → [(DBzB)₄(DOB)₂DOB]₂HOBD (Compound XXVIII)
(2) [(DBzB)₄(DOB)₂DOB]HOBD + (DBzB)₃(BzCBzB)(DOB)₂-DOBBr →
  (DBzB)₇(BzCBzB)(DOB)₄(DOB)₂DOBD (Compound XXIX)
(3) (DBzB)₇(BzCBzB)(DOB)₄(DOB)₂DOBD + (nBu)₄NBH₄ → (DBzB)₇(BzCBzB)(DOB)₄(DOB)₂DOBA (Compound XXX)
(4) (DBzB)₇(BzCBzB)(DOB)₄(DOB)₂DOBA + CBr₄/PPh₃ → (DBzB)₇(BzCBzB)(DOB)₄(DOB)₂DOBBr (Compound XXXI)

Preparation of Dendritic Macromolecules
(1) 2(DBzB)₄(DOB)₂DOBBr + THPE → (DBzB)₈(DOB)₄-(DOB)₂DOHPE (Compound XXXII)
(2) (DBzB)₈(DOB)₄(DOB)₂DOHPE + (DBzB)₃(BzCBzB)-(DOB)₂DOBBr →
  (DBzB)₁₁(BzCBzB)(DOB)₆(DOB)₃TOPE (Compound XXXIII)
(3) (DBzB)₇(BzCBzB)(DOB)₄(DOB)₂DOBBr + TSHPE →
  (DBzB)₇(BzCBzB)(DOB)₄(DOB)₂(DOB)OTHPE (Compound XXXIV)
(4) (DBzB)₇(BzCBzB)(DOB)₄(DOB)₂(DOB)OTHPE + 3(DBzB)₈-(DOB)₄(DOB)₂DOBBr →
  (DBzB)₃₁(BzCBzB)(DOB)₁₆(DOB)₈-(DOB)₄TEOPE (Compound XXXV)

Generation 1

(1) Preparation of BzHBD—Compound XVI (Structure 27 in the Description)

To a mixture of DHBD (24.4 g, 177 mmol) and potassium carbonate (12.2 g, 88.5 mmol) heated at reflux under argon in dry acetone (200 ml) was added dropwise over 12 hours a solution of BzBr (43.4 g, 30.2 ml, 248 mmol) in dry acetone (30 ml). Thin layer chromatography showed very little DHBD after the addition was complete. The reaction mixture was evaporated to dryness and the residue partitioned between dichloromethane/water. The aqueous layer was further extracted with dichloromethane (3×100 ml) and the combined dichloromethane layers extracted with aqueous sodium hydroxide (1N, 3×100 ml). Evaporation of the dichloromethane layers gave 18.1 g of essentially pure 3,5-dibenzyloxybenzaldehyde (34.0% based on DHBD). The sodium hydroxide extracts were acidified with glacial acetic acid, extracted with chloroform (3×100 ml), and the combined chloroform extracts dried and evaporated to dryness. The residue was recrystallized from methanol/water to give 14.5 g of compound XVI (36.0% based on DHBD).

(2) Preparation of BzCBzBD—Compound XVII (Compound 24 in Description)

A mixture of BzHBD (12.0 g, 52.6 mmol), CBzBr (11.3 g, 57.9 mmol), and potassium carbonate (3.46 g, 25.0 mmol) was heated at reflux in dry acetone (100 ml) for 20 hours. The reaction mixture was then evaporated to dryness and the residue partitioned between chloroform/water. The aqueous layer was further extracted with chloroform (3×50 ml) and the combined chloroform extracts dried and evaporated to dryness. The residue was recrystallized from methanol to give 16.1 g of Compound XVII (89% based upon BzHBD).

(3) Preparation of BzCBzBA—Compound XVIII (Compound 25 in Description)

A solution of BzCBzBD (15.0 g, 43.7 mmol) in methanol (300 ml) was heated at reflux under argon while a solution of sodium borohydride (830 mg, 21.9 mmol) in methanol (5 ml) was added dropwise. Thin layer chromatography showed that the reaction had reached completion after addition of the sodium borohydride solution. Water (250 ml) was added and the solution reduced in volume to approx. 300 ml. The product was extracted with chloroform (4×100 ml) and the combined extracts washed with brine (100 ml), dried, and evaporated to dryness. The residue was recrystallized from methanol/water to give 13.7 g of Compound XVIII (91% based on BzCBzBD).

(4) Preparation of BzCBzBBr—Compound XIX (Compound 26 in Description)

This was prepared from BzCBzBA (12.0 g, 34.8 mmol) in dry benzene (70 ml) and phosphorus tribromide (3.33 g, 1.16 ml, 12.3 mmol) in dry benzene (25 ml). The procedure was the same as for DBzBBr (Compound III). The crude product was purified by flash chromatography eluting with chloroform to give 12.1 g of Compound XIX (85% based upon BzCBzBA).

Generation 2

(1) Preparation of (DBzB)HOBD—Compound XX (Compound 27 in Description)

This was prepared from DHBD (10.0 g, 72.5 mmol) and potassium carbonate (5.0 g, 36 mmol) in dry acetone (100 ml) and DBzBBr (Compound III) (38.9 g, 101 mmol) in dry acetone (50 ml). The procedure was the same as for BzHBD (Compound XVI). This gave 13.1 g of Compound XX (41% based on DHBD) which was essentially pure and was used without further purification, 19.9 g of (DBzB)₂DOBD (37% based on DHBD) was also isolated.

(2) Preparation of (DBzB)(BzCBzB)DOBD—Compound XXI (Compound 28 in Description)

This was prepared from (DBzB)HOBD (11.0 g, 250 mmol), BzCBzBBr (10.8 g, 26.5 mmol), and potassium carbonate (3.65 g, 25.0 mmol) in dry acetone (150 ml). The procedure was the same as for (BzCBz)BD (Compound XVII). The crude product was purified by flash chromatography eluting with 10% hexane/chloroform to give 15.7 g of Compound XXI (82% based on (DBzB)HOBD).

(3) Preparation of (DBzB)(BzCBZB)DOBA—Compound XXII

This was prepared from (DBzB)(BzCBzB)DOBD (15.0 g, 19.6 mmol) in methanol (500 ml) and NaBH$_4$ (370 mg, 9.8 mmol) in methanol (5 ml). The procedure was the same as for Compound XVIII. The crude product was purified by flash chromatography eluting with chloroform to give 13.5 g of Compound XXII (90% based upon (DBzB)(BzCBzB)DOBD).

(4) Preparation of (DBzB)(BzCBzB)DOBBr—Compound XXIII

This was prepared from (DBzB)(BzCBzB)DOBA (13.0 g, 16.9 mmol) in dry benzene (100 ml) and phosphorus tribromide (1.62 g, 560 ul, 6.0 mmol) in dry benzene (10 ml). The procedure was the same as for DBzBBr (Compound III). The crude product was purified by flash chromatography eluting with chloroform to give 11.0 g of Compound XXIII (78% based upon (DBzB)(BzCBzB)DOBA.

Generation 3

(1) Preparation of [(DBzB)$_2$DOB]HOBD—Compound XXIV

This was prepared from DHBD (5.00 g, 36.2 mmol), potassium carbonate (2.50 g, 18.0 mmol), and 18-crown-6 (500 mg, 1.9 mmol) in dry dioxane (75 ml) and (DBzB)$_2$DOBBr (Compound VI) (37.6 g, 50.7 mmol) in dry dioxane (50 ml). The procedure was the same as for Compound XVI. After extraction with dichloromethane the combined organic layers were evaporated to dryness and purified by column chromatography eluting with 1:99 ether/chloroform to give 11.9 g of Compound XXIV (38% based on DHBD) and 19.0 g of (DBzB)-(DOB)$_2$DOBD (33% based on DHBD).

(2) Preparation of (DBzB)$_3$(BzCBzB)(DOB)$_2$DOBD—Compound XXV

A mixture of [(DBzB)$_2$DOB]HOBD (11.0 g, 12.7 mmol), (DBzB)(BzCBzB)DOBBr (10.6 g, 12.7 mmol), potassium carbonate (1.82 g, 12.5 mmol), and 18-crown-6 (330 mg, 1.25 mmol) in dry dioxane (100 ml) was heated at reflux under nitrogen for 24 hours. It was then cooled, evaporated to dryness and partitioned between chloroform and water. The aqueous layer is extracted with chloroform (2×50 ml), and the combined organic phases dried and evaporated to dryness. The crude product was purified by flash chromatography eluting with 10% hexane/chloroform to give 16.2 g of Compound XXV (79% based on [(DBzB)$_2$DOB]HOBD).

(3) Preparation of (DBzB)$_3$(BzCBzB)(DOB)$_2$DOBA—Compound XXVI

To a solution of (DBzB)$_3$(BzCBzB)(DOB)$_2$DOBD (15.5 g, 9.60 mmol) dry chloroform (100 ml) was added tetra-n-butylammonium borohydride (1.20 g, 4.43 mmol) and the solution stirred at room temperature under nitrogen for 24 hours. A 3% aqueous solution of hydrogen peroxide (100 ml) was then added and stirring continued for 1 hour. The organic layer was then separated and the aqueous layer extracted with chloroform (2×50 ml). The combined organic layers were then dried and evaporated to dryness. The crude product was purified by flash chromatography eluting with chloroform to give 14.4 g of Compound XXVI (93% based upon (DBzB)$_3$(BzCBzB)(DOB)$_2$DOBD).

(4) Preparation of (DBzB)$_3$(BzCBzB)(DOB)$_2$DOBBr—Compound XXVII

To a stirred solution of (DBzB)$_3$(BzCBzB)(DOB)$_2$DOBA (14.0 g, 8.66 mmol) and carbon tetrabromide (3.31 g, 9.96 mmol) in dry THF (30 ml) was added triphenylphosphine (2.50 g, 9.53 mmol) and stirring continued for 30 minutes. The mixture was then evaporated to dryness and partitioned between chloroform (100 ml) and water (100 ml). The aqueous layer was extracted with chloroform (2×50 ml) and the combined organic layers dried and evaporated to dryness. The crude product was purified by flash chromatography eluting with 20% hexane/chloroform to give 10.8 g of Compound XXVII (74% based upon (DBzB)$_3$(BzCBzB)-(DOB)$_2$DOBA).

Generation 4

(1) Preparation of [(DBzB)$_4$(DOB)$_2$DOB]HOBD—Compound XXVIII

This was prepared from DHBD (4.03 g, 29.2 mmol), potassium carbonate (8.06 g, 58.4 mmol), and 18-crown-6 (1.50 g, 5.7 mmol) in dry dioxane (100 ml) and (DBzB)$_4$(DOB)$_2$DOBBr (16.1 g, 9.73 mmol) in dry dioxane (50 ml). The procedure was the same as for Compound XXIV. The crude product was purified by column chromatography eluting with 2:98 ether/chloroform to give 13.5 g of Compound XXVIII (80% based on (DBzB)$_4$(DOB)$_2$DOBBr).

(2) Preparation of (DBzB)$_7$(BzCBzB)(DOB)$_4$(DOB)$_2$DOBD—Compound XXIX

This was prepared from [(DBxB)$_4$(DOB)$_2$DOB]HOBD (13.0 g, 7.50 mmol), (DBzB)$_3$(BzCBzB)(DOB)$_2$DOBBr (12.5 g, 7.50 mmol), potassium carbonate (2.07 g, 15.0 mmol), and 18-crown-6 (396 mg, 1.50 mmol) in dry dioxane (100 ml). The procedure was the same as for (DBzB)$_3$(BzCBzB)(DOB)DOBD (Compound XXV). The crude product was purified by flash chromatography eluting with 10% hexane/chloroform to give 20.5 g of Compound XXIX (82% based on Compound XXVIII).

(3) Preparation of (DBzB)$_7$(BzCBzB)(DOB)$_4$(DOB)$_2$DOBA—Compound XXX

This was prepared from (DBzB)$_7$(BzCBzB)(DOB)$_4$(DOB)$_2$-DOBD (Compound XXIX) (20.0 g, 6.07 mmol), and tetra-n-butylammonium borohydride (774 mg, 3.0 mmol) in dry chloroform (50 ml). The procedure was the same as for Compound XXVI. The crude product was purified by flash chromatography eluting with chloroform to give 17.1 g of Compound XXX (85% based upon Compound XXIX).

(4) Preparation of (DBzB)$_7$(BzCBzB)(DOB)$_4$(DOB)$_2$DOBBr—Compound XXXI

This was prepared from (DBzB)$_7$(BzCBzB)(DOB)$_4$(DOB)$_2$-DOBA (16.0 g, 4.80 mmol), carbon tetrabromide (2.00 g, 6.02 mmol), and triphenylphosphine (1.45 g, 5.53 mmol) in dry THF (35 ml). The procedure was the same as for Compound XXVII. The crude product was purified by flash chromatography eluting with 10% hexane/chloroform to give 14.10 g of Compound XXI (86% based upon Compound XXX).

Preparation of Dendritic Macromolecule (1) Preparation of (DBzB)$_8$(DOB)$_4$(DOB)$_2$DOH-PE—Compound XXVIII (Compound 29 C in Description)

A solution of (DBzB)$_4$(DOB)$_2$DOBBr (Compound IX) (3.00 g, 1.89 mmol) in dry acetone (20 ml) was added dropwise over 12 hours to a mixture of THPE (287 mg, 0.95 mmol), and potassium carbonate (138 mg, 1.00 mmol) in dry acetone (50 ml) which was heated at reflux under argon. The reaction mixture was then evaporated to dryness and the residue partitioned between water/chloroform. The aqueous layer was further extracted with chloroform (3×50 ml) and the combined chloroform layers dried and evaporated to dryness. The residue was purified by flash chromatography elucitng with 5% hexane/chloroform to give 1.45 g of Compound XXVIII (44% based on THPE).

(2) Preparation of $(DBzB)_{11}(BzCBzB)(DOB)_6$-$(DOB)_3TOPE$—Compound XXIX

A mixture of $(DBzB)_8(DOB)_4(DOB)_2DOHPE$ (1.25 g, 0.36 mmol), $(DBzB)_3(BzCBzB)(DOB)_2DOBBr$ (0.60 g, 0.36 mmol), and potassium carbonate (50 mg, 0.36 mmol) in dry acetone (20 ml) was heated at reflux under argon for 16 hours. The reaction mixture was then evaporated to dryness and the residue partitioned between chloroform/water. The aqueous layer was further extracted with chloroform (3×20 ml) and the combined chloroform extracts dried and evaporated to dryness. The residue was purified by flash chromatography eluting with 10% hexane/chloroform to give 1.39 g of Compound XXIX (76% based upon $(DBzB)_3(BzCBzB)(DOB)_2DOBBr$).

EXAMPLE III

Preparation of Protected Core (24)

A mixture of 1,1,2,2-tetra(4-hydroxyphenyl)ethane (4.00 g, 10.0 mmol) t-butyldimethylsilyl chloride (7.50 g, 50.0 mmol), and imidazole (6.80 g, 100 mmol) is dissolved in dry dimethylformamide (25 ml) and stirred at room temperature under nitrogen for 24 hrs. The mixture is then evaporated to dryness and the residue is partitioned between chloroform (50 ml) and water (50 ml). The aqueous layer is extracted with chloroform (2×25 ml) and the organic layers combined. The residue is dissolved in dry THF (50 ml) and 6 ml of 20% tetra-n-butyl ammonium fluoride in THF is added slowly to the solution at −20° C. over 2 hours. Hydrochloric acid (30 ml, 1N) is then added and the solvent removed in vacuo at 0° C. The residue is extracted with ether and the combined extracts washed with water and brine and dried. The mixture is purified by flash chromatography, eluent is chloroform and the product (24) is obtained in 64% yield.

EXAMPLE IV

Preparation of Monofunctionalized Dendritic Macromolecule (1)

The following procedure was used to prepare dendritic macromolecule (1) in which X is CN: a mixture of the monofunctionalized bromide (33) (3.37 g, 1.00 mmol), protected core (24) of Example III (925 mg, 1.24 mmol), potassium carbonate (170 mg, 1.25 mmol), and 18-crown-6 (33 mg, 0.12 mmol) is dissolved in dry dioxane (25 ml) and is heated at reflux under nitrogen for 24 hours. The mixture is then cooled, evaporated to dryness and partitioned between chloroform (50 ml) and water (50 ml). The aqueous layer is extracted with chloroform (2×25 ml), the combined organic layers dried and the solvent is removed under reduced pressure. The residue is purified by flash chromatography eluting with chloroform/hexane 19:1 to give (34), (3.67 g, 91%). Then (34) (3.50 g, 0.87 mmol) is dissolved in dry tetrahydrofuran (25 ml) and 7.2 ml of 20% tetra-n-butylammonium fluoride in tetrahydrofuran is added slowly to the solution at −20° C. over 2 hours. Acetic acid (10 ml, 2N) is then added and the solvent removed at 0° C. The residue is extracted with chloroform (4×50 ml) and the combined extracts washed with water (50 ml) and brine (50 ml) and dried. The crude product is purified by flash chromatography, eluent is chloroform ether (19:1), to give the triphenol (2.89 g, 90%).

A mixture of the triphenol (2.80 g, 0.7 mmol), the bromide (15) (7.90 g, 2.36 mmol), potassium carbonate (345 mg, 2.50 mmol), and 18-crown-6 (66 mg, 0.25 mmol) is dissolved in dry dioxane and is heated at reflux under nitrogen for 24 hours. The mixture is then cooled, evaporated to dryness and partitioned between chloroform (2×25 ml), the combined organic layers dried and the solvent is removed under reduced pressure. The residue is purified by flash chromatography eluting with chloroform/hexane 19:1 to give (1) (8.30 g, 81%).

EXAMPLE V

Modification of Surface Functional Group and Preparation of Monofunctionalized Dendritic Macromolecule (1A) (X=$CO_2H$)

The cyano-substituted macromolecule (1) of Example IV (1.35 g, 0.10 mmol) is suspended in dioxane/water (1:5) (50 ml) and sodium hydroxide (1.0 g, 25.0 mmol) added. The mixture is then heated at reflux under nitrogen for 10 hours, cooled and evaporated to dryness. Water (50 ml) is added, followed by aqueous HCl (50 ml, 1N) and the mixture is extracted with chloroform (5×25 ml). The combined extracts are dried and evaporated to dryness. The residue is purified by flash chromatography eluting with chloroform giving the acid (1A) (1.18 g, 87%).

EXAMPLE VI

Preparation of "Barbell" Macromolecule

The mono-acid substituted macromolecule (1A) of Example V (1.00 g, 0.074 mmol) is dissolved in dry chloroform (20 ml) and stirred at room temperature under nitrogen, N,N'-carbonyl diimidazole (18.0 mg, 0.12 mmol) is added and stirring continued for 15 minutes. A solution of heptaethylene glycol (12.1 mg, 0.037 mmol) in chloroform (2 ml) is added and stirring continued for 24 hours. Solution is poured into water (50 ml) and is extracted with chloroform (4×20 ml). The combined extracts are washed with water (50 ml) and is extracted with chloroform (4×20 ml). The combined extracts are washed with water (50 ml), dried and evaporated to dryness. The residue is purified by flash chromatography, eluent is chloroform. The "Barbell" macromolecule is thus obtained (615 mg, 61%).

EXAMPLE VII

Preparation of Difunctionalized Dendritic Macromolecule (2)

Dendritic macromolecule (2) in which both X's are cyano is prepared as follows: a mixture of the monofunctionalized bromide (33) (3.37 g, 1.00 mmol), 1,2-bis(4-t-butyldimethylsilyloxy phenyl)-1,2-bis(4-hydroxyphenyl)ethane (313 mg, 0.50 mmol), potassium carbonate (170 mg, 1.25 mmol), and 18-crown-6 (33 mg, 0.12 mmol) is dissolved in dry dioxane (25 ml) and is heated at reflux under nitrogen for 24 hours. The mixture is cooled, evaporated to dryness and partitioned between chloroform (50 ml) and water (50 ml). The aqueous layer is extracted with chloroform (2×25 ml), the combined organic layers dried, and the solvent is removed under reduced pressure. The residue is purified by flash chromatography, eluent is chloroform/hexane, 19:1, the dicyano compound is thus obtained (3.25 g, 85%).

The dicyano compound (3.20 g, 0.84 mmol) is dissolved in dry tetrahydrofuran (25 ml) and 7.2 ml of 20% tetra-n-butylammonium fluoride in tetrahydrofuran is added slowly to the solution at −20° C. over 2 hours. Acetic acid (10 ml, 2N) is then added and the solvent removed at 0° C. The residue is extracted with chloroform (4×25 ml), the combined extracts washed with water (50 ml) and brine (50 ml) and dried. The crude product is purified by flash chromatography, eluent is chloroform/ether 19:1, to give the diphenol (2.76 g, 92%).

A mixture of the diphenol (2.70 g, 0.40 mmol), bromide (15) (2.64 g, 0.80 mmol), potassium carbonate (138 mg, 1.00 mmol), and 18-crown-6 (27 mg, 0.10 mmol) is dissolved in dry dioxane and heated at reflux under nitrogen for 24 hours. The mixture is cooled, evaporated to dryness and partitioned between chloroform (100 ml) and water (50 ml). The aqueous layer is extracted with chloroform (2×25 ml), the combined organic layers dried and the solvent is removed under reduced pressure. The residue is purified by flash chromatography eluting with chloroform/hexane 19:1 to give (2) (4.40 g, 84%).

EXAMPLE VIII

Preparation of Difunctionalized Dendritic Macromolecule (2A)

To prepare a difunctional dendritic macromolecule in which the functional groups are carboxylic acid groups, the dicyano macromolecule (2) (2.70 g, 0.20 mmol) is suspended in dioxane/water (1:5) (50 ml) and sodium hydroxide (2.0 g, 50 mmol) added. The mixture is then heated at reflux under nitrogen for 10 hrs, cooled and evaporated to dryness. Water (50 ml) is added followed by aqueous HCl (50 ml, 1N) and the mixture extracted with chloroform (5×25 ml). The combined extracts are dried and evaporated to dryness. The residue is purified by flash chromatography eluting with chloroform/ether 99:1 to give the diacid (2A) (1.88 g, 70%).

EXAMPLE IX

Preparation of "Knot" Copolymer

The diacid macromolecule (2A) of Example 8 (1.00 g, 0.074 mmol) is dissolved in dry chloroform (20 ml) and stirred at room temperature under nitrogen, N,N'-carbonyldiimidazole (36.0 mg, 0.24 mmol) is added and stirring continued for 15 minutes. A solution of heptaethylene glycol (24.2 mg, 0.074 mmol) in chloroform (2 ml) is added and the solution is heated at reflux under nitrogen for 24 hours. A solution is poured into water (50 ml) is added and the solution is heated at reflux under nitrogen for 24 hours. Solution is poured into water (50 ml) and extracted with chloroform (4×20 ml). The combined extracts are washed with water (50 ml), dried and evaporated to dryness. The residue is dissolved in the minimum amount of chloroform and precipitated into methanol to give the "knot" copolymer as a white solid (780 mg, 76%).

What is claimed is:

1. A process for producing a dendritic macromolecule having a polyfunctional central core connected to a periphery by a dendritic body which comprises building the macromolecule starting with the periphery, continuing through the dendritic body to form a dendritic wedge having a single reacting group at its focal point, and then attaching the wedge through the focal point group to the central core.

2. The process of claim 1, wherein the periphery is comprised of surface compounds having two parts, a non-reacting part and a reacting part.

3. The process of claim 2, wherein the reacting parts of at least two surface compounds are each reacted with a reacting group of a monomer unit which contains at least two of said reacting groups and further contains a non-reacting but activatable group to form the dendritic wedge having a single non-reacting but activatable group at its focal point.

4. The process of claim 3, wherein the non-reacting but activatable focal point groups of at least two dendritic wedges are each activated and reacted with reacting groups of an additional monomer unit to form a larger dendritic wedge having a single non-reacting but activatable group at its focal point.

5. The process of claim 4, wherein the activation of the focal point groups and reacting with reacting groups of additional monomer units is repeated until a dendritic wedge of a predetermined size is prepared.

6. The process of claim 5, wherein at least two dendritic wedges of the predetermined size are attached to the polyfunctional core by activating their respective focal point groups and reacting said groups with reacting groups of the core.

7. The process of claim 1, wherein the non-reacting part of the surface compound contains a reactive group which is non-reacting with all other compounds and reagents used and all intermediates formed in the preparation of the macromolecule.

8. The process of claim 1, wherein the periphery is comprised of at least two different surface compounds.

9. The process of claim 8, wherein the non-reacting part of at least one of the surface compounds contains a reactive group which is non-reacting with all other compounds and reagents used and all intermediates formed in the preparation of the macromolecule.

10. The process of claim 8, wherein the non-reacting parts of at least two of the surface compounds contain different reactive groups each of which is non-reacting with the other and with all other compounds and reagents used and intermediates formed in the preparation of the macromolecule.

11. The process of claim 1, wherein the macromolecule is constructed by (i) reacting a surface compound containing a surface portion which is non-reactive with all compounds and reagents used and intermediates formed in the preparation of the macromolecule and a single group which is reacting with a monomer unit containing at least two groups which are reacting with the reacting group of the surface compound and one group at its focal point which is non-reacting but may be activated to become reacting, (ii) activating the non-reacting focal point group to make it reacting, (iii) reacting the activated focal point group with an additional monomer unit containing a non-reacting group at its focal point, (iv) repeating steps (ii) and (iii) until a dendritic wedge of a predetermined size is formed, (v) activating the non-reacting focal point group of the dendritic wedge and coupling it to a polyfunctional core compound.

12. The process of claim 11, wherein the non-reactive portion of the surface compound contains at least one functional "X" group, wherein "X" is a reactive group which is non-reacting with all compounds and reagents used and intermediates formed in the process, and a reacting group.

13. The process of claim 11, wherein at least two different surface compounds are used to produce the macromolecule.

14. The process of claim 13, wherein the non-reactive portion of at least two of the surface compounds each contains a functional "X" group, wherein "X" is a reactive group which is is non-reacting with all compounds and reagents used and intermediates formed in the process, and which "X" groups are the same or different and are non-reacting with other "X" groups.

15. The process of claim 11 wherein the surface compound is a compound of the formula:

$(s)_m—R—f$ wherein "s" is any group which is non-reacting with any portion of all other compounds and reagents used and all intermediates formed in the preparation of the macromolecule, "m" is an integer, "R" is an organic moiety which is non-reacting with all other compounds and reagents used and intermediates formed in the preparation of the macromolecule, and "f" is a group which is non-reacting with "s" but is reacting with a group "c" of the monomer unit or of the core compound.

16. The process of claim 15, wherein at least one surface compound "s" group is substituted with a reactive "X" group which is non-reacting with all other compounds and reagents used and all intermediates formed in the preparation of the macromolecule.

17. The process of claim 16, wherein "X" is selected from the group consisting essentially of F, Cl, Br, Cn, —NO$_2$, —NHC(O)R$^2$ wherein R$^2$ is alkyl, aryl, O-alkyl, or O-aryl, —CONH$_2$, —CO$_2$R$^3$ wherein R$^3$ is alkyl or aryl, —O—C(O)R$^3$, —OR$^3$, and alkyl or aryl groups substituted with any of the above functional groups.

18. The process of claim 16, wherein "X" is cyano.

19. The process of claim 11, wherein the monomer unit comprises a compound containing (i) at least two groups which are reactive with an activated focal point group of a partially formed dendritic wedge or the reacting group of the surface compound and (ii) a single non-reacting but activatable group at its focal point.

20. The process of claim 11, wherein the monomer unit is a compound of the formula:

$(c)_n—R'—f'$ wherein "c" is a coupling group which is non-reacting with "f" but is reacting with an activated "f" group, "n" is an integer greater than 1, R' is an organic moiety which is non-reacting with all other compounds and reagents used and intermediates formed in the preparation of the macromolecule, and "f" is a non-reacting group which is activatable to form reacting group "f'".

21. The process of claim 11, wherein the core compound is of the formula:

$(c)_x—R''$ wherein "c" is a coupling group which is non-reacting with "f" but is reacting with an activated "f" group, "x" is an integer greater than 1, and "R'''" is any organic moiety which is non-reacting with all other compounds and reagents used and intermediates formed in the preparation of the macromolecule.

22. The process of claim 11, wherein the core compound is of the formula:

$(c)_x—R''$ wherein "c" is a protected coupling group which, after removal of the protection, is non-reacting with "f" but is reacting with an activated "f" group, "x" is an integer greater than 1, and "R''''" is an organic moiety which is non-reacting with all other compounds and reagents used and intermediates formed in the preparation of the macromolecule.

23. A process of forming a dendritic wedge having a single reacting group at its focal point which comprises (i) reacting a surface compound containing a surface group which is non-reacting with all compounds and reagents used and intermediates formed in the preparation of the wedge and a single reacting group which reacts with a monomer unit containing at least two groups which are reacting with the reactive group of the surface compound and one non-reacting group at its focal point, (ii) activating the non-reacting group, (iii) reacting the activated focal point group with an additional monomer unit containing a non-reacting group at its focal point, (iv) repeating steps (ii) and (iii) until a dendritic wedge of the desired size is formed.

24. The process of claim 23, wherein at least two dendritic wedges are produced and each dendritic wedge is coupled to a single core compound having at least two reacting functional sites.

25. The process of claim 23, wherein the dendritic wedge is formed by reacting the surface compound with the monomer unit to form a first generation dendrimer and then reacting at least two of the first generation dendrimers with an identical monomer unit.

26. The process of claim 1 wherein the macromolecule has an outer surface disposed at its periphery which is non-uniformly functionalized having at least one functional group at its outer surface, which functional group is non-reacting with all compounds and reagents used and intermediates formed in preparing the macromolecule.

27. The process of claim 26, wherein the functional group is selected from the group consisting essentially of F, Cl, Br, CN, —NO$_2$, —NHC(O)R$^2$ wherein R$^2$ is alkyl, aryl, O-alkyl, or O-aryl, —CONH$_2$, —CO$_2$R$^3$, —O—C(O)R$^3$, —OR$^3$, wherein R$^3$ is alkyl, aryl, and alkyl and aryl substituted with any of the other functional groups.

28. The process of claim 23, wherein the monomer unit has n coupling sites and one focal non-reactive, activatable focal group and the r'th generation dendritic wedge contains n$^r$ surface compounds which are the same or different.

29. The process of claim 23, wherein the dendritic wedge is constructed by (i) reacting a surface compound containing a surface portion which is non-reacting with all compounds and reagents used and intermediates formed in the preparation of the wedge and a single group which reacts with one of at least two reacting groups of a first monomer unit which further contains one reacting group at its focal point which is non-reacting with the reacting groups of the monomer to form a first generation dendrimer, (ii) reacting the focal point groups of at least two first generation dendrimers with a second monomer unit which is different from the first monomer unit and containing a non-reacting group at its focal point to form a second generation dendrimer, (iii) reacting at least two of the second generation dendrimers with a first monomer unit to form a third generation dendrimer (iv) alternately repeating steps (ii) and (iii) until the dendritic wedge of a predetermined size is formed.

30. A macromolecule comprising a core compound having at least two functional sites and at least one dendritic wedge having a single reacting functional group at its focal point through which it is attached to the core compound, said dendritic wedge having been preformed and then coupled to the core compound by reaction between one of the functional groups on the core compound and the functional group at the focal point of the dendritic wedge.

31. The macromolecules of claim 30 wherein the dendritic wedge has an outer surface disposed at the periphery of the macromolecule in which the outer surface contains at least one functional group which is non-reacting with all compounds and reagents used and intermediates formed in the preparation of the macromolecule.

32. The macromolecule of claim 30, wherein at least two dendritic wedges are coupled to the core compound.

33. The macromolecule of claim 32, wherein at least one of the dendritic wedges is different from the other.

34. The macromolecule of claim 33, wherein the dendritic wedges have outer surfaces disposed at the periphery of the macromolecule in which the outer surfaces differ in the number of functional groups thereon.

35. The macromolecule of claim 34 wherein the functional groups on the outer surface are selected from the group consisting of F, Cl, Br, CN, —NO$_2$, —NH-C(O)R$^2$ wherein R$^2$ is alkyl, aryl, O-alkyl, or O-aryl, —CONH$_2$, —CO$_2$R$^3$, —O—C(O)R$^3$, —OR$^3$, wherein R$^3$ is alkyl or aryl, and alkyl or aryl groups substituted with any of the other functional groups.

36. The macromolecule of claim 35 wherein the functional groups on the outer surface are cyano.

37. The macromolecule of claim 33, wherein the dendritic wedges have outer surfaces disposed at the periphery of the macromolecule in which the outer surfaces differ in the type of functional groups thereon.

38. The macromolecule of claim 37 wherein the functional groups on the outer surface are selected from the group consisting of F, Cl, Br, CN, —NO$_2$, —NH-C(O)R$^2$ wherein R$^2$ is alkyl, aryl, O-alkyl, or O-aryl, —CONH$_2$, —CO$_2$R$^3$, —O—C(O)R$^3$, —OR$^3$, wherein R$^3$ is alkyl or aryl, and alkyl or aryl groups substituted with any of the other functional groups.

39. The macromolecules of claim 38 wherein at least one of the functional groups on the outer surface is cyano.

40. The macromolecule of claim 32, wherein at least one of the dendritic wedges is uniformly functionalized.

41. The macromolecule of claim 30, wherein the dendritic wedge has internal linkage layers which comprise the group

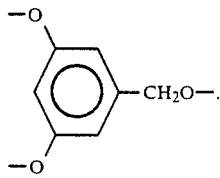

42. The macromolecule of claim 30, wherein the dendritic wedge has internal lingage layers which comprise the group

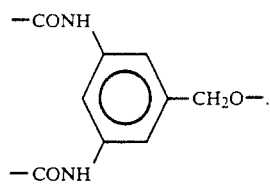

43. The macromolecule of claim 30, wherein the dendritic wedge has internal linkages selected from the group consisting essentially of ether, urethane, ester, carbonate, urea, and amide linkages.

44. The macromolecule of claim 30, wherein the core compound is selected from the group consisting of compounds of the formula:

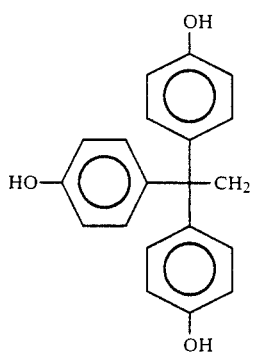

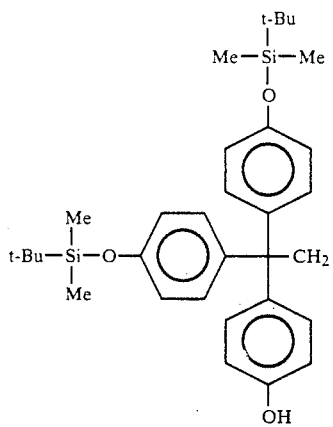

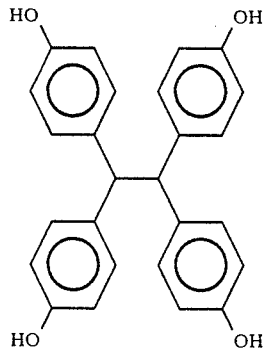

-continued

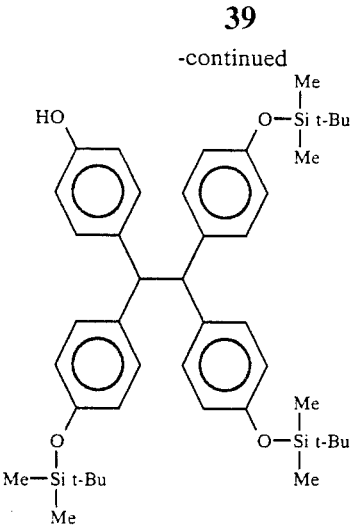

pentaerythritol, pyromellitic anhydride, glucose, phloroglucinol, pyromellitic acid, benzenetetracarboxylic acid and anhydride, and ethylenediamine.

45. The macromolecule of claim 30, wherein the core compound is a polymer.

46. A dendrimer comprising a highly branched polymer chain which contains a single reacting group located at its focal point.

47. The dendrimer of claim 46, wherein said dendrimer is a non-uniformly functionalized molecule having at least one functional group at its outer surface which functional group is non-reacting with all compounds and reagents used and intermediates formed in the preparation of the dendrimer.

48. The dendrimer of claim 47, wherein the functional group is selected from the group consisting essentially of F, Cl, Br, CN, $-NO_2$, $-NHC(O)R^2$ wherein $R^2$ is alkyl, aryl, O-alkyl, or O-aryl, $-CONH_2$, $-CO_2R^3$, $-O-C(O)R^3$, $-OR^3$, wherein $R^3$ is alkyl or aryl, and alkyl or aryl groups substituted with any of the other functional groups.

49. The dendrimer of claim 47, wherein the functional group is cyano.

50. The dendrimer of claim 46 containing internal linkage layers comprising the group

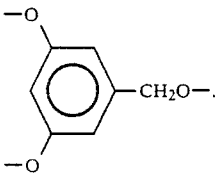

51. The dendrimer of claim 46, containing internal linkage layers comprising the group

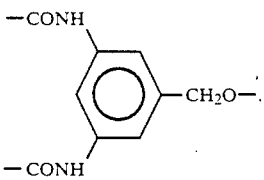

52. The dendrimer of claim 46 containing internal linkages selected from the group consisting essentially of ether, urethane, ester, carbonate, urea, and amide linkages.

* * * * *